United States Patent
Puhl et al.

(10) Patent No.: US 7,767,624 B2
(45) Date of Patent: Aug. 3, 2010

(54) 3-HETEROCYCLYL SUBSTITUTED BENZOIC ACID DERIVATIVES

(75) Inventors: Michael Puhl, Lampertheim (DE); Gerhard Hamprecht, Weinheim (DE); Robert Reinhard, Ludwigshafen (DE); Ingo Sagasser, Dannstadt-Schauernheim (DE); Werner Seitz, Plankstadt (DE); Cyrill Zagar, Mannheim (DE); Matthias Witschel, Bad Dürkheim (DE); Andreas Landes, Römerberg-Heiligenstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1532 days.

(21) Appl. No.: 10/522,095

(22) PCT Filed: Jul. 22, 2003

(86) PCT No.: PCT/EP03/08013

§ 371 (c)(1),
(2), (4) Date: Jan. 24, 2005

(87) PCT Pub. No.: WO2004/009561

PCT Pub. Date: Jan. 29, 2004

(65) Prior Publication Data

US 2005/0239655 A1    Oct. 27, 2005

(30) Foreign Application Priority Data

Jul. 23, 2002    (DE) .................. 102 33 402

(51) Int. Cl.
*A01N 43/46* (2006.01)
*A01N 43/56* (2006.01)
*A01N 43/54* (2006.01)
*C07D 237/00* (2006.01)
*C07D 213/72* (2006.01)

(52) U.S. Cl. .................. 504/227; 544/309; 544/239; 544/222; 546/290; 504/236; 504/243; 504/254

(58) Field of Classification Search .................. 544/311, 544/312, 313, 239, 309, 222; 504/243, 168, 504/227, 236; 546/590

See application file for complete search history.

(56) References Cited

U.S. PATENT DOCUMENTS

| | | | |
|---|---|---|---|
| 4,859,229 A * | 8/1989 | Wenger et al. | ............... 504/243 |
| 4,941,909 A | 7/1990 | Wenger et al. | |
| 5,017,211 A | 5/1991 | Wenger et al. | |
| 5,041,156 A | 8/1991 | Suchy et al. | |
| 5,183,492 A | 2/1993 | Suchy et al. | |
| 6,057,269 A * | 5/2000 | Klintz et al. | ................. 504/243 |
| 6,239,074 B1 | 5/2001 | Klintz et al. | |

FOREIGN PATENT DOCUMENTS

| | | |
|---|---|---|
| WO | WO 92/06962 A1 | 4/1992 |
| WO | WO 98/28280 A1 | 7/1998 |
| WO | WO 01/83459 A2 | 11/2001 |
| WO | WO 03/029226 A1 | 4/2003 |

OTHER PUBLICATIONS

Dorwald F. A. Side Reactions in Organic Synthesis, 2005, Wiley: VCH, Weinheim p. IX of Preface.*

* cited by examiner

*Primary Examiner*—Sabiha Qazi
(74) *Attorney, Agent, or Firm*—Rothwell, Figg, Ernst & Manbeck, P.C.

(57) ABSTRACT

Disclosed are 3-heterocyclyl substituted benzoic acid derivatives of general formula (I),

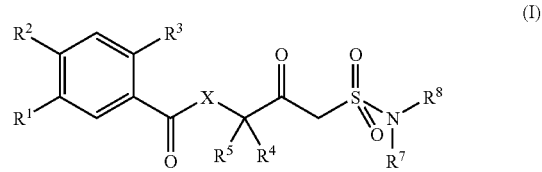

in which the variables $R^1$ to $R^8$ and X have the meanings indicated in claim 1, and the use thereof as herbicides or for desiccating/defoliating plants.

16 Claims, No Drawings

3-HETEROCYCLYL SUBSTITUTED BENZOIC ACID DERIVATIVES

CROSS REFERENCE TO RELATED APPLICATION

This application is a 35 USC §371 National Phase Entry Application from PCT/EP2003/008013, filed Jul. 22, 2003, and designating the U.S.

The present invention relates to 3-heterocyclyl-substituted benzoic acid derivatives and their agriculturally useful salts, to compositions comprising such compounds and to the use of the 3-heterocyclyl-substituted benzoic acid derivatives, of their salts or of compositions comprising them as herbicides, desiccants or defoliants.

In various publications, uracil-substituted benzoic acid derivatives have been described as herbicidally active compounds. Thus, for example, WO 88/10254, WO 89/03825 and WO 91/00278 describe the esters of 2-halo-5-(substituted uracil)benzoic acids and the esters of 2-cyano-5-(substituted uracil)benzoic acids which may optionally be halogen-substituted in the 4-position. WO 89/02891 and WO 93/06090 describe the amides of 2-halo-5-(substituted uracil)benzoic acids and the amides of 2-cyano-5-(substituted uracil)benzoic acids which may optionally be halogen-substituted in the 4-position, as herbicidally active substances.

Furthermore, WO 01/83459 discloses herbicidally active 3-heterocyclyl-substituted phenylsulfamoylcarboxamides of the formula A

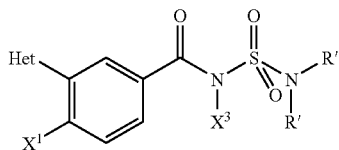

A where Het is, inter alia, an unsaturated five- or six-membered heterocyclic radical which is attached via a nitrogen atom to the phenyl ring, $X^1$ is hydrogen, halogen or $C_1$-$C_4$-alkyl, $X^2$ is hydrogen, cyano, thiocarbamoyl, halogen, $C_1$-$C_4$-alkyl or $C_1$-$C_4$-haloalkyl, $X^3$ is, inter alia, hydrogen, $C_1$-$C_6$-alkyl, $C_1$-$C_6$-alkoxyalkyl, R' are each independently of one another inter alia hydrogen, alkoxy, $C_1$-$C_{10}$-alkyl, $C_2$-$C_{10}$-alkenyl, $C_3$-$C_{10}$-alkynyl, $C_3$-$C_7$-cycloalkyl, or the two radicals R' together with the nitrogen atom to which they are attached form a 3- to 7-membered heterocyclic ring.

It is an object of the present invention to provide novel herbicidally active compounds which allow better targeted control of unwanted plants than the known herbicides. Advantageously, the novel herbicides should be highly active against harmful plants. Moreover, a high compatibility with crop plants is desirable. It is another object to provide novel compounds having desiccant/defoliant action.

We have found, surprisingly, that these objects are achieved by 3-heterocyclyl-substituted benzoic acid derivatives of the general formula I defined below:

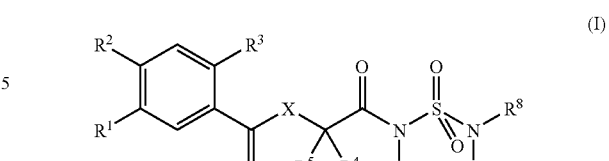

(I)

where:
X is oxygen or $NR^9$,
$R^1$ is a heterocyclic radical of the formulae II-A to II-H,

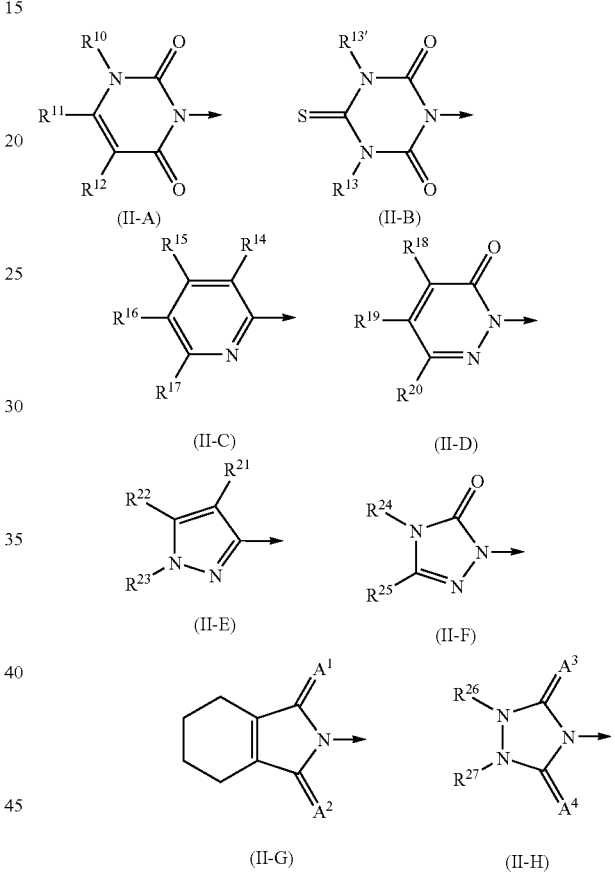

$R^2$ is hydrogen or halogen,
$R^3$ is halogen or cyano,
$R^4$, $R^5$ independently of one another are hydrogen, $C_1$-$C_4$-alkyl or $C_1$-$C_4$-alkoxy, or $R^4$ and $R^5$ together are a group =$CH_2$,
$R^6$ is hydrogen, $C_1$-$C_4$-alkyl or $C_1$-$C_4$-alkoxy,
$R^7$, $R^8$ independently of one another are hydrogen, $C_1$-$C_6$-alkyl, $C_3$-$C_6$-alkenyl, $C_3$-$C_6$-alkynyl, $C_1$-$C_4$-haloalkyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl, cyano-$C_1$-$C_4$-alkyl, $C_1$-$C_4$-alkoxycarbonyl-$C_1$-$C_4$-alkyl, amino-$C_1$-$C_4$-alkyl, $C_1$-$C_4$-alkylamino-$C_1$-$C_4$-alkyl, di($C_1$-$C_4$-alkyl)amino-$C_1$-$C_4$-alkyl, aminocarbonyl-$C_1$-$C_4$-alkyl, ($C_1$-$C_4$-alkylamino)carbonyl-$C_1$-$C_4$-alkyl, di($C_1$-$C_4$-alkyl)aminocarbonyl-$C_1$-$C_4$-alkyl, phenyl or $C_1$-$C_4$-alkylphenyl or
$R^7$ and $R^8$ together with the nitrogen atom to which they are attached form a saturated or unsaturated 3-, 4-, 5-, 6- or 7-membered nitrogen heterocycle which may optionally contain one or two further heteroatoms selected from the group consisting of nitrogen, sulfur and oxygen as ring members, which may contain 1 or 2 carbonyl and/or thiocarbonyl groups as ring members and/or which may be substituted by one, two or three substituents selected from the group consisting of $C_1$-$C_4$-alkyl and halogen;

$R^9$ is hydrogen, hydroxyl, $C_1$-$C_4$-alkyl, $C_1$-$C_4$-alkoxy, phenyl, phenyl-$C_1$-$C_4$-alkyl, $C_3$-$C_6$-alkenyl or $C_3$-$C_6$-alkynyl, $R^{10}$ is hydrogen, $C_1$-$C_4$-alkyl or amino, $R^{11}$ is $C_1$-$C_4$-alkyl or $C_1$-$C_4$-haloalkyl, $R^{12}$ is hydrogen or $C_1$-$C_4$-alkyl, $R^{13}$, $R^{13'}$ independently of one another are hydrogen or $C_1$-$C_4$-alkyl, $R^{14}$ is halogen, $R^{15}$ is hydrogen or $C_1$-$C_4$-alkyl, $R^{16}$ is $C_1$-$C_4$-haloalkyl, $C_1$-$C_4$-alkylthio, $C_1$-$C_4$-alkylsulfonyl or $C_1$-$C_4$-alkylsulfonyloxy, $R^{17}$ is hydrogen or $C_1$-$C_4$-alkyl, $R^{18}$ is hydrogen, $C_1$-$C_4$-alkyl or amino, $R^{19}$ is $C_1$-$C_4$-haloalkyl, $C_1$-$C_4$-alkylthio or $C_1$-$C_4$-alkylsulfonyl.

$R^{20}$ is hydrogen or $C_1$-$C_4$-alkyl, $R^{21}$ is hydrogen, halogen or $C_1$-$C_4$-alkyl, $R^{22}$ is $C_1$-$C_4$-alkyl, $C_1$-$C_4$-haloalkyl, $C_1$-$C_4$-haloalkoxy, $C_1$-$C_4$-alkylthio or $C_1$-$C_4$-alkylsulfonyl, $R^{23}$ is hydrogen or $C_1$-$C_4$-alkyl, or $R^{22}$ and $R^{23}$ together with the atoms to which they are attached form a 5-, 6- or 7-membered saturated or unsaturated ring which may contain a heteroatom selected from the group consisting of oxygen and nitrogen as a ring-forming atom and/or which may be substituted by one, two or three radicals selected from the group consisting of $C_1$-$C_4$-alkyl and halogen, $R^{24}$ is hydrogen, $C_1$-$C_4$-alkyl or $C_1$-$C_4$-haloalkyl, $R^{25}$ is $C_1$-$C_4$-alkyl or $C_1$-$C_4$-haloalkyl, or $R^{24}$ and $R^{25}$ together with the atoms to which they are attached form a 5-, 6- or 7-membered saturated or unsaturated ring which optionally contains an oxygen atom as ring-forming atom and/or which may be substituted by one, two or three radicals selected from the group consisting of $C_1$-$C_4$-alkyl and halogen, $R^{26}$ is hydrogen, $C_1$-$C_4$-alkyl or $C_1$-$C_4$-haloalkyl, $R^{27}$ is hydrogen, $C_1$-$C_4$-alkyl or $C_1$-$C_4$-haloalkyl, or $R^{26}$ and $R^{27}$ together with the atoms to which they are attached form a 5-, 6- or 7-membered saturated or unsaturated ring which optionally contains an oxygen atom as ring-forming atom and/or which may be substituted by one, two or three radicals selected from the group consisting of $C_1$-$C_4$-alkyl and halogen, $A^1$, $A^2$, $A^3$, $A^4$ are each independently of one another oxygen or sulfur.

Accordingly, the present invention relates to 3-heterocyclyl-substituted benzoic acid derivatives of the formula I and their agriculturally useful salts.

The invention also relates to the tautomers of the compounds I, for example to compounds I in which $R^1$ is a heterocyclic radical of the formula II-A, II-B, II-F or II-H.

Moreover, the present invention relates to the use of the compounds I and/or their salts as herbicides or for the desiccation/defoliation of plants herbicidal compositions comprising the compounds I and/or their salts as active substances, compositions for the dessication/defoliation of plants, which compositions comprise the compounds I and/or their salts as active substances, and also methods for controlling unwanted vegetation or for the desiccation/defoliation of plants using the compounds I and/or their salts.

Depending on the substitution pattern, the compounds of the formula I may contain one or more centers of chirality, in which case they are present as mixtures of enantiomers or diastereomers. The invention provides both the pure enantiomers or diastereomers and mixtures thereof.

Agriculturally useful salts are especially the salts of those cations or the acid addition salts of those acids whose cations and anions, respectively, have no adverse effect on the herbicidal action and/or desiccant/defoliant action of the compounds I. Thus, particularly suitable cations are the ions of the alkali metals, preferably sodium and potassium, of the alkaline earth metals, preferably calcium, magnesium and barium, and of the transition metals, preferably manganese, copper, zinc and iron, and also the ammonium ion, which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, hydrogencarbonate, carbonate, hexafluorosilicate, hexafluorophosphate, benzoate, and also the anions of $C_1$-$C_4$-alkanoic acids, preferably formate, acetate, propionate and butyrate. They can be formed by reacting I with an acid of the corresponding anion, preferably hydrochloric acid, hydrobromic acid, sulfuric acid, phosphoric acid or nitric acid.

The organic moieties mentioned in the definition of the substituents $R^1$ to $R^{27}$ or as radicals on heterocyclic rings are—like the term halo—collective terms of individual listings of the individual group members. All carbon chains, i.e. all alkyl, haloalkyl, cyanoalkyl, aminoalkyl, aminocarbonylalkyl, alkoxy, haloalkoxy, alkylthio, haloalkylthio, alkylsulfinyl, alkylsulfonyl, alkylsulfonyloxy and alkenyl moieties may be straight-chain or branched. Halogenated substituents preferably carry one to five identical or different halogen atoms. The term halogen denotes in each case fluorine, chlorine, bromine or iodine.

Examples of other meanings are:

$C_1$-$C_4$-alkyl: for example methyl, ethyl, propyl, 1-methylethyl, butyl, 1-methylpropyl, 2-methylpropyl or 1,1-dimethylethyl;

$C_1$-$C_6$-alkyl: $C_1$-$C_4$-alkyl as mentioned above and also, for example n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$-$C_4$-haloalkyl: a $C_1$-$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl; in particular difluoromethyl, trifluoromethyl;

$C_1$-$C_4$-alkoxy: for example methoxy, ethoxy, n-propoxy, 1-methylethoxy, butoxy, 1-methylpropoxy, 2-methylpropoxy or 1,1-dimethylethoxy;

$C_1$-$C_4$-haloalkoxy: a $C_1$-$C_4$-alkoxy radical as mentioned above which is partially or fully substituted by fluorine, chlorine, bromine and/or iodine, i.e. for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$;

$C_1$-$C_4$-alkoxy-$C_1$-$C_4$-alkyl: $C_1$-$C_4$-alkyl which is substituted by $C_1$-$C_4$-alkoxy as mentioned above, i.e., for example, $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl;

$C_1$-$C_4$-alkylthio: for example $SCH_3$, $SC_2H_5$, $SCH_2$—$C_2H_5$, $SCH(CH_3)_2$, n-butylthio, $SCH(CH_3)$—$C_2H_5$, $SCH_2$—$CH(CH_3)_2$ or $SC(CH_3)_3$;

$C_1$-$C_4$-alkylthio-$C_1$-$C_4$-alkyl: $C_1$-$C_4$-alkyl, which is substituted by $C_1$-$C_4$-alkylthio as mentioned above, i.e., for example, $CH_2$—$SCH_3$, $CH_2$—$HC_2H_5$, n-propylthiomethyl, $CH_2$—$SCH(CH_3)_2$, n-butylthiomethyl, (1-methylpropylthio)methyl, (2-methylpropylthio)methyl, $CH_2$—$SC(CH_3)_3$, 2-(methylthio)ethyl, 2-(ethylthio)ethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 2-(ethylthio)propyl, 2-(n-propylthio)propyl, 2-(1-methylethylthio)propyl, 2-(n-butylthio)propyl, 2-(1-methylpropylthio)propyl, 2-(2-methylpropylthio)propyl, 2-(1,1-dimethylethylthio)propyl, 3-(methylthio)propyl, 3-(ethylthio)propyl, 3-(n-propylthio)propyl, 3-(1-methylethylthio)propyl, 3-(n-butylthio)propyl, 3-(1-methylpropylthio)propyl, 3-(2-methylpropylthio)propyl, 3-(1,1-dimethylethylthio)propyl, 2-(methylthio)butyl, 2-(ethylthio)butyl, 2-(n-propylthio)butyl, 2-(1-methylethylthio)butyl, 2-(n-butylthio)butyl, 2-(1-methylpropylthio)butyl, 2-(2-methylpropylthio)butyl, 2-(1,1-dimethylethylthio)butyl, 3-(methylthio)butyl, 3-(ethylthio)butyl, 3-(n-propylthio)butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-(methylthio)butyl, 4-(ethylthio)butyl, 4-(n-propylthio)butyl, 4-(1-methylethylthio)butyl, 4-(n-butylthio)butyl, 4-(1-methylpropylthio)butyl, 4-(2-methylpropylthio)butyl or 4-(1,1-dimethylethylthio)butyl;

$C_1$-$C_4$-alkylsulfinyl ($C_1$-$C_4$-alkyl-S(=O)—) and the alkylsulfinyl moieties of $C_1$-$C_4$-alkylsulfinyl-$C_1$-$C_4$-alkyl: for example methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl;

$C_1$-$C_4$-alkylsulfonyl ($C_1$-$C_4$-alkyl-S(=O)$_2$—) and the alkylsulfonyl moieties of $C_1$-$C_4$-alkylsulfonyl-$C_1$-$C_4$-alkyl: for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl, preferably methylsulfonyl;

$C_1$-$C_4$-alkylsulfonyloxy: for example methylsulfonyloxy, ethylsulfonyloxy, n-propylsulfonyloxy, 1-methylethylsulfonyloxy, butylsulfonyloxy, 1-methylpropylsulfonyloxy, 2-methylpropylsulfonyloxy or 1,1-dimethylethylsulfonyloxy, preferably methylsulfonyloxy;

cyano-$C_1$-$C_4$-alkyl: for example $CH_2CN$, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-($CH_2CN$)eth-1-yl, 1-($CH_2CN$)-1-($CH_3$)eth-1-yl or 1-($CH_2CN$)prop-1-yl;

phenyl-$C_1$-$C_4$-alkyl: for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(benzyl)eth-1-yl, 1-(benzyl)-1-(methyl)eth-1-yl or 1-(benzyl)prop-1-yl;

$C_1$-$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

($C_1$-$C_4$-alkoxy)carbonyl-$C_1$-$C_4$-alkyl: $C_1$-$C_4$-alkyl which is substituted by ($C_1$-$C_4$-alkoxy)carbonyl as mentioned above, i.e., for example, $CH_2$—CO—$OCH_3$, $CH_2$—CO—$OC_2H_5$, $CH_2$—CO—$OCH_2$—$C_2H_5$, $CH_2$—

CO—OCH(CH$_3$)$_2$, n-butoxycarbonylmethyl, CH$_2$—CO—OCH(CH$_3$)—C$_2$H$_5$, CH$_2$—CO—OCH$_2$—CH(CH$_3$)$_2$, CH$_2$—CO—OC(CH$_3$)$_3$, 1-(CO—OCH$_3$) ethyl, 1-(CO—OC$_2$H$_5$) ethyl, 1-(CO—OCH$_2$—C$_2$H$_5$)ethyl, 1-[CO—OCH(CH$_3$)$_2$]ethyl, 1-(n-butoxycarbonyl) ethyl, 1-[1-methylpropoxycarbonyl]ethyl, 1-[2-methylpropoxycarbonyl]ethyl, 2-(CO—OCH$_3$)ethyl, 2-(CO—OC$_2$H$_5$) ethyl, 2-(CO—OCH$_2$—C$_2$H$_5$) ethyl, 2-[CO—OCH(CH$_3$)$_2$]ethyl, 2-(n-butoxycarbonyl)ethyl, 2-[1-methylpropoxycarbonyl]ethyl, 2-[2-methylpropoxycarbonyl]ethyl, 2-[CO—OC(CH$_3$)$_3$]ethyl, 2-(CO—OCH$_3$)propyl, 2-(CO—OC$_2$H$_5$)propyl, 2-(CO—OCH$_2$—C$_2$H$_5$) propyl, 2-[CO—OCH(CH$_3$)$_2$]propyl, 2-(n-butoxycarbonyl) propyl, 2-[1-methylpropoxycarbonyl]propyl, 2-[2-methylpropoxycarbonyl]propyl, 2-[CO—OC(CH$_3$)$_3$]propyl, 3-(CO—OCH$_3$)propyl, 3-(CO—OC$_2$H$_5$)propyl, 3-(CO—OCH$_2$—C$_2$H$_5$) propyl, 3-[CO—OCH(CH$_3$)$_2$]propyl, 3-(n-butoxycarbonyl)propyl, 3-[1-methylpropoxycarbonyl]propyl, 3-[2-methylpropoxycarbonyl]propyl, 3-[CO—OC(CH$_3$)$_3$]propyl, 2-(CO—OCH$_3$)butyl, 2-(CO—OC$_2$H$_5$)butyl, 2-(CO—OCH$_2$—C$_2$H$_5$)butyl, 2-[CO—OCH(CH$_3$)$_2$]butyl, 2-(n-butoxycarbonyl)butyl, 2-[1-methylpropoxycarbonyl]butyl, 2-[2-methylpropoxycarbonyl]butyl, 2-[CO—OC(CH$_3$)$_3$]butyl, 3-(CO—OCH$_3$)butyl, 3-(CO—OC$_2$H$_5$)butyl, 3-(CO—OCH$_2$—C$_2$H$_5$)butyl, 3-[CO—OCH(CH$_3$)$_2$]butyl, 3-(n-butoxycarbonyl)butyl, 3-[1-methylpropoxycarbonyl]butyl, 3-[2-methylpropoxycarbonyl]butyl, 3-[CO—OC(CH$_3$)$_3$]butyl, 4-(CO—OCH$_3$)butyl, 4-(CO—OC$_2$H$_5$)butyl, 4-(CO—OCH$_2$—C$_2$H$_5$)butyl, 4-[CO—OCH(CH$_3$)$_2$]butyl, 4-(n-butoxycarbonyl)butyl, 4-[1-methylpropoxycarbonyl]butyl, 4-[2-methylpropoxycarbonyl]butyl or 4-[CO—OC(CH$_3$)$_3$]butyl, preferably CH$_2$—CO—OCH$_3$, CH$_2$—CO—OC$_2$H$_5$, 1-(CO—OCH$_3$) ethyl or 1-(CO—OC$_2$—H$_5$) ethyl;

amino-C$_1$-C$_4$-alkyl: for example CH$_2$NH$_2$, 1-aminoethyl, 2-aminoethyl, 1-aminoprop-1-yl, 2-aminoprop-1-yl, 3-aminoprop-1-yl, 1-aminobut-1-yl, 2-aminobut-1-yl, 3-aminobut-1-yl, 4-aminobut-1-yl, 1-aminobut-2-yl, 2-aminobut-2-yl, 3-aminobut-2-yl, 4-aminobut-2-yl, 1-(CH$_2$NH$_2$) eth-1-yl, 1-(CH$_2$NH$_2$)-1-(CH$_3$) eth-1-yl or 1-(CH$_2$NH$_2$) prop-1-yl;

C$_1$-C$_4$-alkylamino: for example H$_3$C—NH—, H$_5$C$_2$—NH—, n-propyl-NH—, 1-methyl ethyl-NH-, n-butyl-NH-, 1-methylpropyl-NH-, 2-methylpropyl-NH— or 1,1-dimethylethyl-NH—;

C$_1$-C$_4$-alkylamino-C$_1$-C$_4$-alkyl: C$_1$-C$_4$-alkyl which is substituted by C$_1$-C$_4$-alkylamino as defined above, i.e., for example, CH$_2$CH$_2$—NH—CH$_3$, CH$_2$CH$_2$—N(CH$_3$)$_2$, CH$_2$CH$_2$—NH—C$_2$H$_5$ or CH$_2$CH$_2$—N(C$_2$H$_5$)$_2$;

di(C$_1$-C$_4$-alkyl)amino: N(CH$_3$)$_2$, N(C$_2$H$_5$)$_2$, N,N-dipropylamino, N,N-di(1-methylethyl)amino, N,N-dibutylamino, N,N-di(1-methylpropyl)amino, N,N-di-(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl) amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)-amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di(C$_1$-C$_4$-alkyl)amino-C$_1$-C$_4$-alkyl: C$_1$-C$_4$-alkyl which is substituted by di(C$_1$-C$_4$-alkyl)amino as mentioned above, i.e., for example, CH$_2$N(CH$_3$)$_2$, CH$_2$N(C$_2$H$_5$)$_2$, N,N-dipropylaminomethyl, N,N-di[CH(CH$_3$)$_2$]aminomethyl, N,N-dibutylaminomethyl, N,N-di(1-methylpropyl)aminomethyl, N,N-di(2-methylpropyl)aminomethyl, N,N-di[C(CH$_3$)$_3$]aminomethyl, N-ethyl-N-methylaminomethyl, N-methyl-N-propylaminomethyl, N-methyl-N—[CH(CH$_3$)$_2$]aminomethyl, N-butyl-N-methylaminomethyl, N-methyl-N-(1-methylpropyl)aminomethyl, N-methyl-N-(2-methylpropyl)aminomethyl, N—[C(CH$_3$)$_3$]-N-methylaminomethyl, N-ethyl-N-propylaminomethyl, N-ethyl-N—[CH(CH$_3$)$_2$]aminomethyl, N-butyl-N-ethylaminomethyl, N-ethyl-N-(1-methylpropyl)aminomethyl, N-ethyl-N-(2-methylpropyl)aminomethyl, N-ethyl-N—[C(CH$_3$)$_3$]aminomethyl, N—[CH(CH$_3$)$_2$]-N-propylaminomethyl, N-butyl-N-propylaminomethyl, N-(1-methylpropyl)-N-propylaminomethyl, N-(2-methylpropyl)-N-propylaminomethyl, N—[C(CH$_3$)$_3$]-N-propylaminomethyl, N-butyl-N-(1-methylethyl)-aminomethyl, N—(CH(CH$_3$)$_2$]-N-(1-methylpropyl)aminomethyl, N—[CH(CH$_3$)$_2$]-N-(2-methylpropyl)aminomethyl, N—[C(CH$_3$)$_3$]-N—[CH(CH$_3$)$_2$]aminomethyl, N-butyl-N-(1-methylpropyl)aminomethyl, N-butyl-N-(2-methylpropyl)aminomethyl, N-butyl-N—[C(CH$_3$)$_3$]aminomethyl, N-(1-methylpropyl)-N-(2-methylpropyl)aminomethyl, N—[C(CH$_3$)$_3$]-N-(1-methylpropyl)aminomethyl, N—[C(CH$_3$)$_3$]-N-(2-methylpropyl)aminomethyl, N,N-dimethylaminoethyl, N,N-diethylaminoethyl, N,N-di(n-propyl)aminoethyl, N,N-di[CH(CH$_3$)$_2$]-aminoethyl, N,N-dibutylaminoethyl, N,N-di(1-methylpropyl)aminoethyl, N,N-di(2-methylpropyl)aminoethyl, N,N-di[C(CH$_3$)$_3$]aminoethyl, N-ethyl-N-methylaminoethyl, N-methyl-N-propylaminoethyl, N-methyl-N—[CH(CH$_3$)$_2$]aminoethyl, N-butyl-N-methylaminoethyl, N-methyl-N-(1-methylpropyl)aminoethyl, N-methyl-N-(2-methylpropyl)aminoethyl, N—[C(CH$_3$)$_3$]-N-methylaminoethyl, N-ethyl-N-propylaminoethyl, N-ethyl-N—[CH(CH$_3$)$_2$]aminoethyl, N-butyl-N-ethylaminoethyl, N-ethyl-N-(1-methylpropyl)aminoethyl, N-ethyl-N-(2-methylpropyl)aminoethyl, N-ethyl-N—[C(CH$_3$)$_3$]aminoethyl, N—[CH(CH$_3$)$_2$]-N-propylaminoethyl, N-butyl-N-propylaminoethyl, N-(1-methylpropyl)-N-propylaminoethyl, N-(2-methylpropyl)-N-propylaminoethyl, N—[C(CH$_3$)$_3$]-N-propylaminoethyl, N-butyl-N—[CH(CH$_3$)$_2$]aminoethyl, N—[CH(CH$_3$)$_2$]-N-(1-methylpropyl)aminoethyl, N—[CH(CH$_3$)$_2$]-N-(2-methylpropyl)aminoethyl, N—[C(CH$_3$)$_3$]-N—[CH(CH$_3$)$_2$]aminoethyl, N-butyl-N-(1-methylpropyl)aminoethyl, N-butyl-N-(2-methylpropyl)aminoethyl, N-butyl-N—[C(CH$_3$)$_3$]aminoethyl, N-(1-methylpropyl)-N-(2-methylpropyl)aminoethyl, N—[C(CH$_3$)$_3$]-N-(1-methylpropyl)aminoethyl or N—[C(CH$_3$)$_3$]-N-(2-methylpropyl)aminoethyl;

aminocarbonyl-C$_1$-C$_4$-alkyl: for example CH$_2$CONH$_2$, 1-(CONH$_2$)ethyl, 2-(CONH$_2$)ethyl, 1-(CONH$_2$)prop-1-yl, 2-(CONH$_2$)prop-1-yl, 3-(CONH$_2$)prop-1-yl, 1-(CONH$_2$)but-1-yl, 2-(CONH$_2$)but-1-yl, 3-(CONH$_2$) but-1-yl, 4-(CONH$_2$)but-1-yl, 1-(CONH$_2$)but-2-yl, 2-(CONH$_2$)but-2-yl, 3-(CONH$_2$)but-2-yl, 4-(CONH$_2$) but-2-yl, 1-(CH$_2$CONH$_2$)eth-1-yl, 1-(CH$_2$CONH$_2$)-1-(CH$_3$)-eth-1-yl or 1-(CH$_2$CONH$_2$)prop-1-yl;

($C_1$-$C_4$-alkylamino)carbonyl-$C_1$-$C_4$-alkyl: $C_1$-$C_4$-alkyl which is substituted by ($C_1$-$C_4$-alkylamino)carbonyl as mentioned above, i.e., for example, CH$_2$—CO—NH—CH$_3$, CH$_2$—CO—NH—C$_2$H$_5$, CH$_2$—CO—NH—CH$_2$—C$_2$H$_5$, CH$_2$—CO—NH—CH(CH$_3$)$_2$, CH$_2$—CO—NH—CH$_2$CH$_2$—C$_2$H$_5$, CH$_2$—CO—NH—CH(CH$_3$)—C$_2$H$_5$, CH$_2$—CO—NH—CH$_2$—CH(CH$_3$)$_2$, CH$_2$—CO—NH—C(CH$_3$)$_3$, CH(CH$_3$)—CO—NH—CH$_3$, CH(CH$_3$)—CO—NH—C$_2$H$_5$, 2-(CO—NH—CH$_3$)ethyl, 2-(CO—NH—C$_2$H$_5$)ethyl, 2-(CO—NH—CH$_2$—C$_2$H$_5$)ethyl, 2-[CH$_2$—CO—NH—CH(CH$_3$)$_2$]ethyl, 2-(CO—NH—CH$_2$CH$_2$—C$_2$H$_5$)ethyl, 2-[CO—NH—CH(CH$_3$)—C$_2$H$_5$]ethyl, 2-[CO—NH—CH$_2$—CH(CH$_3$)$_2$]ethyl, 2-[CO—NH—C(CH$_3$)$_3$]ethyl, 2-(CO—NH—CH$_3$)propyl, 2-(CO—NH—C$_2$H$_5$)propyl, 2-(CO—NH—CH$_2$—C$_2$H$_5$)propyl, 2-[CH$_2$—CO—NH—CH(CH$_3$)$_2$]propyl, 2-(CO—NH—CH$_2$CH$_2$—C$_2$H$_5$)propyl, 2-[CO—NH—CH(CH$_3$)—C$_2$H$_5$]propyl, 2-[CO—NH—CH$_2$—CH(CH$_3$)$_2$]propyl, 2-[CO—NH—C(CH$_3$)$_3$]propyl, 3-(CO—NR—CH$_3$)propyl, 3-(CO—NH—C$_2$H$_5$)propyl, 3-(CO—NH—CH$_2$—C$_2$H$_5$)propyl, 3-[CH$_2$—CO—NH—CH(CH$_3$)$_2$]propyl, 3-(CO—NH—CH$_2$CH$_2$—C$_2$H$_5$)propyl, 3-[CO—NH—CH(CH$_3$)—C$_2$H$_5$]propyl, 3-[CO—NH—CH$_2$—CH(CH$_3$)$_2$]Propyl 3-[CO—NH—C(CH$_3$)$_3$]propyl, 2-(CO—NH—CH$_3$)butyl, 2-(CO—NH—C$_2$H$_5$)butyl, 2-(CO—NH—CH$_2$—C$_2$H$_5$)butyl, 2-[CH$_2$—CO—NH—CH(CH$_3$)$_2$]butyl, 2-(CO—NH—CH$_2$CH$_2$—C$_2$H$_5$)butyl, 2-[CO—NH—CH(CH$_3$)—C$_2$H$_5$]butyl, 2-[CO—NH—CH$_2$—CH(CH$_3$)$_2$]butyl, 2-[CO—NH—C(CH$_3$)$_3$]butyl, 3-(CO—NH—CH$_3$)butyl, 3-(CO—NH—C$_2$H$_5$)butyl, 3-(CO—NH—CH$_2$—C$_2$H$_5$)butyl, 3-[CH$_2$—CO—NH—CH(CH$_3$)$_2$]butyl, 3-(CO—NH—CH$_2$CH$_2$—C$_2$H$_5$)butyl, 3-[CO—NH—CH(CH$_3$)—C$_2$H$_5$]butyl, 3-[CO—NH—CH$_2$—CH(CH$_3$)$_2$]butyl, 3-[CO—NH—C(CH$_3$)$_3$]butyl, 4-(CO—NH—CH$_3$)butyl, 4-(CO—NH—C$_2$H$_5$)butyl, 4-(CO—NH—CH$_2$—C$_2$H$_5$)butyl, 4-[CH$_2$—CO—NH—CH(CH$_3$)$_2$]butyl, 4-(CO—NH—CH$_2$CH$_2$—C$_2$H$_5$)butyl, 4-[CO—NH—CH(CH$_3$)—C$_2$H$_5$]butyl, 4-[CO—NH—CH$_2$—CH(CH$_3$)$_2$]butyl or 4-[CO—NH—C(CH$_3$)$_3$]butyl, di($C_1$-$C_4$-alkyl)aminocarbonyl-$C_1$-$C_4$-alkyl: $C_1$-$C_4$-alkyl which is substituted by di($C_1$-$C_4$-alkyl)aminocarbonyl as mentioned above, i.e., for example, di($C_1$-$C_4$-alkyl) aminocarbonylmethyl, 1- or 2-di($C_1$-$C_4$-alkyl)aminocarbonylethyl, 1-, 2- or 3-di($C_1$-$C_4$-alkyl)aminocarbonylpropyl;

$C_1$-$C_4$-alkylphenyl: phenyl which is substituted by $C_1$-$C_4$-alkyl as mentioned above, i.e., for example, 2-tolyl, 3-tolyl, 4-tolyl, 2-ethylphenyl, 3-ethylphenyl, 4-ethylphenyl, 2-(n-propyl)phenyl, 3-(n-propyl)phenyl, 4-(n-propyl)phenyl, 2-(1-methylethyl)phenyl, 3-(1-methylethyl)phenyl, 4-(1-methylethyl)phenyl, 2-(n-butyl) phenyl, 3-(n-butyl)phenyl, 4-(n-butyl)phenyl, 2-(1-methylpropyl)phenyl, 3-(1-methylpropyl)phenyl, 4-(1-methylpropyl)phenyl, 2-(2-methylpropyl)phenyl, 3-(2-methylpropyl)phenyl, 4-(2-methylpropyl)phenyl, 2-(1,1-dimethylethyl)phenyl, 3-(1,1-dimethylethyl)phenyl, 4-(1,1-dimethylethyl)phenyl;

$C_3$-$C_6$-alkenyl: a monounsaturated aliphatic hydrocarbon radical having 3 to 6 carbon atoms which is preferably not attached via an olefinic carbon atom, for example prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_3$-$C_6$-alkynyl: an aliphatic hydrocarbon radical which contains a triple bond and 3 to 6 carbon atoms and which is preferably not attached via a carbon atom of the triple bond, for example propargyl (2-propynyl), 1-propynyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl.

With respect to the use of the compounds of the formula I according to the invention as herbicides or as compounds with desiccant/defoliant action, the variables X, $R^2$ to $R^6$ are preferably as defined below, in each case independently of one another and in particular in combination:

X is oxygen, $R^2$ is hydrogen, fluorine or chlorine, $R^3$ is chlorine or cyano, in particular chlorine, $R^4$, $R^5$ independently of one another are hydrogen or $C_1$-$C_4$-alkyl, in particular hydrogen or methyl, $R^6$ is hydrogen or $C_1$-$C_4$-alkyl, in particular hydrogen or methyl.

In a preferred embodiment of the invention, $R^4$ or $R^5$ is hydrogen and the other radical $R^4$ or $R^5$ is $C_1$-$C_4$-alkyl, in particular methyl or $R^4$, $R^5$ are each methyl.

Very particular preference is given to compounds of the formula I where $R^2$ is hydrogen, chlorine or fluorine, $R^3$ is chlorine or cyano, $R^6$ is hydrogen and X is oxygen.

Particular emphasis is given to the following embodiments of the 3-heterocyclyl-substituted benzoic acid derivatives of the formula I:

1. In a particularly preferred embodiment, $R^1$ in formula I is a heterocyclic radical of the formula II-A. Hereinbelow, such compounds are also referred to as compounds I-A. In the compounds I-A, X and $R^2$ to $R^8$ preferably and in particular have the meanings mentioned as being preferred and particularly preferred, respectively. In particular, in formula II-A, $R^{10}$ is $C_1$-$C_4$-alkyl or amino, in particular methyl or amino,
   $R^{11}$ is $C_1$-$C_4$-haloalkyl, in particular trifluoromethyl, and
   $R^{12}$ is hydrogen.

2. In a further preferred embodiment, $R^1$ in formula I is a heterocyclic radical of the formula II-B. Hereinbelow, such compounds are also referred to as compounds I-B. In the compounds I-B, X and $R^2$ to $R^8$ preferably and in particular have the meanings given as being preferred and particularly preferred, respectively. In particular, in formula. II-B.
   $R^{13}$, $R^{13'}$ are each independently of one another $C_1$-$C_4$-alkyl, in particular methyl.

3. In a further preferred embodiment, $R^1$ in formula I is a heterocyclic radical of the formula II-C. Hereinbelow, such compounds are also referred to as compounds I-C. In the compounds I-C, X and $R^2$ to $R^8$ preferably and in particular have the meanings given as being preferred and particularly preferred, respectively. In particular, in formula II-C,
   $R^{14}$ is fluorine or chlorine, in particular chlorine,
   $R^{15}$ is hydrogen or $C_1$-$C_4$-alkyl, in particular hydrogen,
   $R^{16}$ is $C_1$-$C_4$-haloalkyl, $C_1$-$C_4$-alkylsulfonyl or $C_1$-$C_4$-alkylsulfonyloxy, in particular trifluoromethyl, methylsulfonyl or methylsulfonyloxy.

4. In a further preferred embodiment, $R^1$ in formula I is a heterocyclic radical of the formula II-D. Hereinbelow, such compounds are also referred to as compounds I-D. In the compounds I-D, X and $R^2$ to $R^8$ preferably and in particular have the meanings given as being preferred and particularly preferred, respectively. In particular, in formula II-D,
   $R^{18}$ is hydrogen, methyl or amino,
   $R^{19}$ is $C_1$-$C_4$-haloalkyl or $C_1$-$C_4$-alkylsulfonyl, in particular trifluoromethyl or methylsulfonyl,
   $R^{20}$ is hydrogen.

5. In a further preferred embodiment, $R^1$ in formula I is a heterocyclic radical of the formula II-E. Hereinbelow, such compounds are also referred to as compounds I-E. In the compounds I-E, X and $R^2$ to $R^8$ preferably and in particular have the meanings given as being preferred and particularly preferred, respectively. In particular, in formula II-E,
   $R^{21}$ is halogen or $C_1$-$C_4$-alkyl, in particular chlorine or bromine,
   $R^{22}$ is $C_1$-$C_4$-haloalkyl, $C_1$-$C_4$-haloalkoxy or $C_1$-$C_4$-alkylsulfonyl, in particular trifluoromethyl, difluoromethyloxy or methylsulfonyl,
   $R^{23}$ is $C_1$-$C_4$-alkyl, in particular methyl.

6. In a further preferred embodiment, $R^1$ in formula I is a heterocyclic radical of the formula II-F. Hereinbelow, such compounds are also referred to as compounds I-F. In the compounds I-F, X and $R^2$ to $R^8$ preferably and in particular have those meanings which have been mentioned as being preferred and particularly preferred, respectively. In particular in formula II-F,
   $R^{24}$ is hydrogen, methyl, difluoromethyl or trifluoromethyl,
   $R^{25}$ is methyl or trifluoromethyl,
   or
   $R^{24}$ and $R^{25}$ together are a chain of the formula —$(CH_2)_4$—.

7. In a further preferred embodiment, $R^1$ in formula I is a heterocyclic radical of the formula II-G. Hereinbelow, such compounds are also referred to as compounds I-G. In the compounds I-G, X and $R^2$ to $R^8$ preferably and in particular have the meanings given as being preferred and particularly preferred, respectively. In particular, in formula II-G, $A^1$, $A^2$ are each oxygen.

8. In a further preferred embodiment, $R^1$ in formula I is a heterocyclic radical of the formula II-H. Hereinbelow, such compounds are also referred to as compounds I-H. In the compounds I-H, X and $R^2$ to $R^8$ preferably and in particular have those meanings which have been mentioned as preferred and particularly preferred, respectively. In particular, in formula II-H,
   $A^3$, $A^4$ are as defined above and are preferably each oxygen,
   $R^{26}$, $R^{27}$ are each independently of one another $C_1$-$C_4$-alkyl or $C_1$-$C_4$-haloalkyl, in particular methyl or difluoromethyl or trifluoromethyl, or
   $R^{26}$ and $R^{27}$ together are a chain of the formula —$CH_2$—O—$(CH_2)_2$— or —$(CH_2)_4$—.

Very particular preference is given to the compounds of the formula I, where $R^1$ is II-A where $R^{10}$=$CH_3$ or amino, $R^{11}$=$CF_3$ and $R^{12}$=hydrogen, $R^2$ is hydrogen or fluorine, $R^3$ is chlorine or cyano, $R^6$ is hydrogen and X is oxygen.

Very particular preference is given to the 3-heterocyclyl-substituted benzoic acid derivatives of the formula I-Aa (≡I where $R^1$=II-A, $R^{10}$=methyl, $R^{11}$=trifluoromethyl and $R^{12}$=hydrogen, $R^2$=F, $R^3$=Cl, $R^6$=H, X=O), where $R^4$, $R^5$, $R^7$ and $R^8$ have the meanings mentioned above, in particular the meanings mentioned as being preferred. Examples of such compounds are the compounds I-Aa.1 to I-Aa.600 in which the variables $R^4$, $R^5$, $R^7$ and $R^8$ together have the meanings given in one row of Table 1.

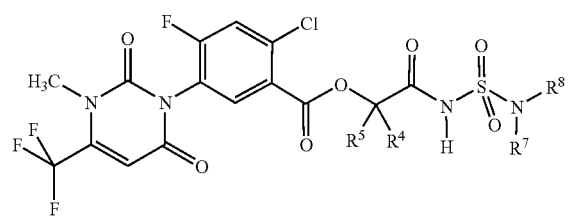

(I-Aa)

TABLE 1

| No. | R⁴ | R⁵ | R⁷ | R⁸ |
|---|---|---|---|---|
| 1 | H | H | H | H |
| 2 | H | H | H | CH₃ |
| 3 | H | H | H | CH₂CH₃ |
| 4 | H | H | H | CH₂CH₂CH₃ |
| 5 | H | H | H | CH₂CH₂CH₂CH₃ |
| 6 | H | H | H | CH(CH₃)₂ |
| 7 | H | H | H | CH₂CH(CH₃)₂ |
| 8 | H | H | H | CH(CH₃)CH₂CH₃ |
| 9 | H | H | H | C(CH₃)₃ |
| 10 | H | H | H | CH₂OCH₃ |
| 11 | H | H | H | CH₂CH₂OCH₃ |
| 12 | H | H | H | CH₂OCH₂CH₃ |
| 13 | H | H | H | CH₂CH₂OCH₂CH₃ |
| 14 | H | H | H | CH(CH₃)CH₂OCH₃ |
| 15 | H | H | H | CH₂CH₂Cl |
| 16 | H | H | H | CH₂CH₂SCH₃ |
| 17 | H | H | H | CH₂CH₂S(O)CH₃ |
| 18 | H | H | H | CH₂CH₂S(O)₂CH₃ |
| 19 | H | H | H | CH₂CH₂CN |
| 20 | H | H | H | CH₂CH₂CO₂CH₃ |
| 21 | H | H | H | CH₂CH₂CO₂CH₂CH₃ |
| 22 | H | H | H | CH₂CH₂NH₂ |
| 23 | H | H | H | CH₂CH₂N(CH₃)₂ |
| 24 | H | H | H | CH₂CH₂N(CH₂CH₃)₂ |
| 25 | H | H | H | CH₂CH=CH₂ |
| 26 | H | H | H | C(CH₃)=CH₂ |
| 27 | H | H | H | CH₂CH=CHCH₃ |
| 28 | H | H | H | C(CH₃)CH=CHCH₃ |
| 29 | H | H | H | CH₂C≡CH |
| 30 | H | H | H | CH(CH₃)C≡CH |
| 31 | H | H | H | CH₂C≡CHCH₃ |
| 32 | H | H | H | Ph |
| 33 | H | H | —(CH₂)₄— | |
| 34 | H | H | —(CH₂)₅— | |
| 35 | H | H | —(CH₂)₂NH(CH₂)₂— | |
| 36 | H | H | —(CH₂)₂NCH₃(CH₂)₂— | |
| 37 | H | H | —(CH₂)₂O(CH₂)₂— | |
| 38 | H | H | —CH₂CH=CHCH₂— | |
| 39 | H | H | —CH=CHCH₂CH₂— | |
| 40 | H | H | —CH=CHCH₂CH₂— | |
| 41 | H | H | CH₃ | H |
| 42 | H | H | CH₃ | CH₃ |
| 43 | H | H | CH₃ | CH₂CH₃ |
| 44 | H | H | CH₃ | CH₂CH₂CH₃ |
| 45 | H | H | CH₃ | CH₂CH₂CH₂CH₃ |
| 46 | H | H | CH₃ | CH(CH₃)₂ |
| 47 | H | H | CH₃ | CH₂CH(CH₃)₂ |
| 48 | H | H | CH₃ | CH(CH₃)CH₂CH₃ |
| 49 | H | H | CH₃ | C(CH₃)₃ |
| 50 | H | H | CH₃ | CH₂OCH₃ |
| 51 | H | H | CH₃ | CH₂CH₂OCH₃ |
| 52 | H | H | CH₃ | CH₂OCH₂CH₃ |
| 53 | H | H | CH₃ | CH₂CH₂OCH₂CH₃ |
| 54 | H | H | CH₃ | CH(CH₃)CH₂OCH₃ |
| 55 | H | H | CH₃ | CH₂CH₂Cl |
| 56 | H | H | CH₃ | CH₂CH₂SCH₃ |
| 57 | H | H | CH₃ | CH₂CH₂S(O)CH₃ |
| 58 | H | H | CH₃ | CH₂CH₂S(O)₂CH₃ |
| 59 | H | H | CH₃ | CH₂CH₂CN |
| 60 | H | H | CH₃ | CH₂CH₂CO₂CH₃ |
| 61 | H | H | CH₃ | CH₂CH₂CO₂CH₂CH₃ |
| 62 | H | H | CH₃ | CH₂CH₂NH₂ |
| 63 | H | H | CH₃ | CH₂CH₂N(CH₃)₂ |
| 64 | H | H | CH₃ | CH₂CH₂N(CH₂CH₃)₂ |
| 65 | H | H | CH₃ | CH₂CH=CH₂ |
| 66 | H | H | CH₃ | C(CH₃)=CH₂ |
| 67 | H | H | CH₃ | CH₂CH=CHCH₃ |
| 68 | H | H | CH₃ | C(CH₃)CH=CHCH₃ |
| 69 | H | H | CH₃ | CH₂C≡CH |
| 70 | H | H | CH₃ | CH(CH₃)C≡CH |
| 71 | H | H | CH₃ | CH₂C≡CHCH₃ |
| 72 | H | H | CH₃ | Ph |
| 73 | H | H | CH₂CH₃ | H |
| 74 | H | H | CH₂CH₃ | CH₃ |
| 75 | H | H | CH₂CH₃ | CH₂CH₃ |
| 76 | H | H | CH₂CH₃ | CH₂CH₂CH₃ |
| 77 | H | H | CH₂CH₃ | CH₂CH₂CH₂CH₃ |
| 78 | H | H | CH₂CH₃ | CH(CH₃)₂ |
| 79 | H | H | CH₂CH₃ | CH₂CH(CH₃)₂ |
| 80 | H | H | CH₂CH₃ | CH(CH₃)CH₂CH₃ |
| 81 | H | H | CH₂CH₃ | C(CH₃)₃ |
| 82 | H | H | CH₂CH₃ | CH₂OCH₃ |
| 83 | H | H | CH₂CH₃ | CH₂CH₂OCH₃ |
| 84 | H | H | CH₂CH₃ | CH₂OCH₂CH₃ |
| 85 | H | H | CH₂CH₃ | CH₂CH₂OCH₂CH₃ |
| 86 | H | H | CH₂CH₃ | CH(CH₃)CH₂OCH₃ |
| 87 | H | H | CH₂CH₃ | CH₂CH₂Cl |
| 88 | H | H | CH₂CH₃ | CH₂CH₂SCH₃ |
| 89 | H | H | CH₂CH₃ | CH₂CH₂S(O)CH₃ |
| 90 | H | H | CH₂CH₃ | CH₂CH₂S(O)₂CH₃ |
| 91 | H | H | CH₂CH₃ | CH₂CH₂CN |
| 92 | H | H | CH₂CH₃ | CH₂CH₂CO₂CH₃ |
| 93 | H | H | CH₂CH₃ | CH₂CH₂CO₂CH₂CH₃ |
| 94 | H | H | CH₂CH₃ | CH₂CH₂NH₂ |
| 95 | H | H | CH₂CH₃ | CH₂CH₂N(CH₃)₂ |
| 96 | H | H | CH₂CH₃ | CH₂CH₂N(CH₂CH₃)₂ |
| 97 | H | H | CH₂CH₃ | CH₂CH=CH₂ |
| 98 | H | H | CH₂CH₃ | C(CH₃)=CH₂ |
| 99 | H | H | CH₂CH₃ | CH₂CH=CHCH₃ |
| 100 | H | H | CH₂CH₃ | C(CH₃)CH=CHCH₃ |
| 101 | H | H | CH₂CH₃ | CH₂C≡CH |
| 102 | H | H | CH₂CH₃ | CH(CH₃)C≡CH |
| 103 | H | H | CH₂CH₃ | CH₂C≡CHCH₃ |
| 104 | H | H | CH₂CH₃ | Ph |
| 105 | H | H | CH₂CH₂CH₃ | H |
| 106 | H | H | CH₂CH₂CH₃ | CH₃ |
| 107 | H | H | CH₂CH₂CH₃ | CH₂CH₃ |
| 108 | H | H | CH₂CH₂CH₃ | CH₂CH₂CH₃ |
| 109 | H | H | CH₂CH₂CH₃ | CH₂CH₂CH₂CH₃ |
| 110 | H | H | CH₂CH₂CH₃ | CH(CH₃)₂ |
| 111 | H | H | CH₂CH₂CH₃ | CH₂CH(CH₃)₂ |
| 112 | H | H | CH₂CH₂CH₃ | CH(CH₃)CH₂CH₃ |
| 113 | H | H | CH₂CH₂CH₃ | C(CH₃)₃ |
| 114 | H | H | CH₂CH₂CH₃ | CH₂OCH₃ |
| 115 | H | H | CH₂CH₂CH₃ | CH₂CH₂OCH₃ |
| 116 | H | H | CH₂CH₂CH₃ | CH₂OCH₂CH₃ |
| 117 | H | H | CH₂CH₂CH₃ | CH₂CH₂OCH₂CH₃ |
| 118 | H | H | CH₂CH₂CH₃ | CH(CH₃)CH₂OCH₃ |
| 119 | H | H | CH₂CH₂CH₃ | CH₂CH₂Cl |
| 120 | H | H | CH₂CH₂CH₃ | CH₂CH₂SCH₃ |
| 121 | H | H | CH₂CH₂CH₃ | CH₂CH₂S(O)CH₃ |
| 122 | H | H | CH₂CH₂CH₃ | CH₂CH₂S(O)₂CH₃ |
| 123 | H | H | CH₂CH₂CH₃ | CH₂CH₂CN |
| 124 | H | H | CH₂CH₂CH₃ | CH₂CH₂CO₂CH₃ |
| 125 | H | H | CH₂CH₂CH₃ | CH₂CH₂CO₂CH₂CH₃ |
| 126 | H | H | CH₂CH₂CH₃ | CH₂CH₂NH₂ |
| 127 | H | H | CH₂CH₂CH₃ | CH₂CH₂N(CH₃)₂ |
| 128 | H | H | CH₂CH₂CH₃ | CH₂CH₂N(CH₂CH₃)₂ |
| 129 | H | H | CH₂CH₂CH₃ | CH₂CH=CH₂ |
| 130 | H | H | CH₂CH₂CH₃ | C(CH₃)=CH₂ |
| 131 | H | H | CH₂CH₂CH₃ | CH₂CH=CHCH₃ |
| 132 | H | H | CH₂CH₂CH₃ | C(CH₃)CH=CHCH₃ |
| 133 | H | H | CH₂CH₂CH₃ | CH₂C≡CH |
| 134 | H | H | CH₂CH₂CH₃ | CH(CH₃)C≡CH |
| 135 | H | H | CH₂CH₂CH₃ | CH₂C≡CHCH₃ |
| 136 | H | H | CH₂CH₂CH₃ | Ph |
| 137 | H | H | CH(CH₃)₂ | H |
| 138 | H | H | CH(CH₃)₂ | CH₃ |
| 139 | H | H | CH(CH₃)₂ | CH₂CH₃ |
| 140 | H | H | CH(CH₃)₂ | CH₂CH₂CH₃ |
| 141 | H | H | CH(CH₃)₂ | CH₂CH₂CH₂CH₃ |
| 142 | H | H | CH(CH₃)₂ | CH(CH₃)₂ |
| 143 | H | H | CH(CH₃)₂ | CH₂CH(CH₃)₂ |
| 144 | H | H | CH(CH₃)₂ | CH(CH₃)CH₂CH₃ |
| 145 | H | H | CH(CH₃)₂ | C(CH₃)₃ |
| 146 | H | H | CH(CH₃)₂ | CH₂OCH₃ |
| 147 | H | H | CH(CH₃)₂ | CH₂CH₂OCH₃ |
| 148 | H | H | CH(CH₃)₂ | CH₂OCH₂CH₃ |
| 149 | H | H | CH(CH₃)₂ | CH₂CH₂OCH₂CH₃ |
| 150 | H | H | CH(CH₃)₂ | CH(CH₃)CH₂OCH₃ |
| 151 | H | H | CH(CH₃)₂ | CH₂CH₂Cl |
| 152 | H | H | CH(CH₃)₂ | CH₂CH₂SCH₃ |
| 153 | H | H | CH(CH₃)₂ | CH₂CH₂S(O)CH₃ |
| 154 | H | H | CH(CH₃)₂ | CH₂CH₂S(O)₂CH₃ |

TABLE 1-continued

| No. | R⁴ | R⁵ | R⁷ | R⁸ |
|---|---|---|---|---|
| 155 | H | H | CH(CH₃)₂ | CH₂CH₂CN |
| 156 | H | H | CH(CH₃)₂ | CH₂CH₂CO₂CH₃ |
| 157 | H | H | CH(CH₃)₂ | CH₂CH₂CO₂CH₂CH₃ |
| 158 | H | H | CH(CH₃)₂ | CH₂CH₂NH₂ |
| 159 | H | H | CH(CH₃)₂ | CH₂CH₂N(CH₃)₂ |
| 160 | H | H | CH(CH₃)₂ | CH₂CH₂N(CH₂CH₃)₂ |
| 161 | H | H | CH(CH₃)₂ | CH₂CH=CH₂ |
| 162 | H | H | CH(CH₃)₂ | C(CH₃)=CH₂ |
| 163 | H | H | CH(CH₃)₂ | CH₂CH=CHCH₃ |
| 164 | H | H | CH(CH₃)₂ | C(CH₃)CH=CHCH₃ |
| 165 | H | H | CH(CH₃)₂ | CH₂C≡CH |
| 166 | H | H | CH(CH₃)₂ | CH(CH₃)C≡CH |
| 167 | H | H | CH(CH₃)₂ | CH₂C≡CCH₃ |
| 168 | H | H | CH(CH₃)₂ | Ph |
| 169 | H | H | CH₂CH=CH₂ | H |
| 170 | H | H | CH₂CH=CH₂ | CH₃ |
| 171 | H | H | CH₂CH=CH₂ | CH₂CH₃ |
| 172 | H | H | CH₂CH=CH₂ | CH₂CH₂CH₃ |
| 173 | H | H | CH₂CH=CH₂ | CH₂CH₂CH₂CH₃ |
| 174 | H | H | CH₂CH=CH₂ | CH(CH₃)₂ |
| 175 | H | H | CH₂CH=CH₂ | CH₂CH(CH₃)₂ |
| 176 | H | H | CH₂CH=CH₂ | CH(CH₃)CH₂CH₃ |
| 177 | H | H | CH₂CH=CH₂ | C(CH₃)₃ |
| 178 | H | H | CH₂CH=CH₂ | CH₂OCH₃ |
| 179 | H | H | CH₂CH=CH₂ | CH₂CH₂OCH₃ |
| 180 | H | H | CH₂CH=CH₂ | CH₂OCH₂CH₃ |
| 181 | H | H | CH₂CH=CH₂ | CH₂CH₂OCH₂CH₃ |
| 182 | H | H | CH₂CH=CH₂ | CH(CH₃)CH₂OCH₃ |
| 183 | H | H | CH₂CH=CH₂ | CH₂CH₂Cl |
| 184 | H | H | CH₂CH=CH₂ | CH₂CH₂SCH₃ |
| 185 | H | H | CH₂CH=CH₂ | CH₂CH₂S(O)CH₃ |
| 186 | H | H | CH₂CH=CH₂ | CH₂CH₂S(O)₂CH₃ |
| 187 | H | H | CH₂CH=CH₂ | CH₂CH₂CN |
| 188 | H | H | CH₂CH=CH₂ | CH₂CH₂CO₂CH₃ |
| 189 | H | H | CH₂CH=CH₂ | CH₂CH₂CO₂CH₂CH₃ |
| 190 | H | H | CH₂CH=CH₂ | CH₂CH₂NH₂ |
| 191 | H | H | CH₂CH=CH₂ | CH₂CH₂N(CH₃)₂ |
| 192 | H | H | CH₂CH=CH₂ | CH₂CH₂N(CH₂CH₃)₂ |
| 193 | H | H | CH₂CH=CH₂ | CH₂CH=CH₂ |
| 194 | H | H | CH₂CH=CH₂ | C(CH₃)=CH₂ |
| 195 | H | H | CH₂CH=CH₂ | CH₂CH=CHCH₃ |
| 196 | H | H | CH₂CH=CH₂ | C(CH₃)CH=CHCH₃ |
| 197 | H | H | CH₂CH=CH₂ | CH₂C≡CH |
| 198 | H | H | CH₂CH=CH₂ | CH(CH₃)C≡CH |
| 199 | H | H | CH₂CH=CH₂ | CH₂C≡CCH₃ |
| 200 | H | H | CH₂CH=CH₂ | Ph |
| 201 | CH₃ | H | H | H |
| 202 | CH₃ | H | H | CH₃ |
| 203 | CH₃ | H | H | CH₂CH₃ |
| 204 | CH₃ | H | H | CH₂CH₂CH₃ |
| 205 | CH₃ | H | H | CH₂CH₂CH₂CH₃ |
| 206 | CH₃ | H | H | CH(CH₃)₂ |
| 207 | CH₃ | H | H | CH₂CH(CH₃)₂ |
| 208 | CH₃ | H | H | CH(CH₃)CH₂CH₃ |
| 209 | CH₃ | H | H | C(CH₃)₃ |
| 210 | CH₃ | H | H | CH₂OCH₃ |
| 211 | CH₃ | H | H | CH₂CH₂OCH₃ |
| 212 | CH₃ | H | H | CH₂OCH₂CH₃ |
| 213 | CH₃ | H | H | CH₂CH₂OCH₂CH₃ |
| 214 | CH₃ | H | H | CH(CH₃)CH₂OCH₃ |
| 215 | CH₃ | H | H | CH₂CH₂Cl |
| 216 | CH₃ | H | H | CH₂CH₂SCH₃ |
| 217 | CH₃ | H | H | CH₂CH₂S(O)CH₃ |
| 218 | CH₃ | H | H | CH₂CH₂S(O)₂CH₃ |
| 219 | CH₃ | H | H | CH₂CH₂CN |
| 220 | CH₃ | H | H | CH₂CH₂CO₂CH₃ |
| 221 | CH₃ | H | H | CH₂CH₂CO₂CH₂CH₃ |
| 222 | CH₃ | H | H | CH₂CH₂NH₂ |
| 223 | CH₃ | H | H | CH₂CH₂N(CH₃)₂ |
| 224 | CH₃ | H | H | CH₂CH₂N(CH₂CH₃)₂ |
| 225 | CH₃ | H | H | CH₂CH=CH₂ |
| 226 | CH₃ | H | H | C(CH₃)=CH₂ |
| 227 | CH₃ | H | H | CH₂CH=CHCH₃ |
| 228 | CH₃ | H | H | C(CH₃)CH=CHCH₃ |
| 229 | CH₃ | H | H | CH₂C≡CH |
| 230 | CH₃ | H | H | CH(CH₃)C≡CH |
| 231 | CH₃ | H | H | CH₂C≡CCH₃ |
| 232 | CH₃ | H | H | Ph |
| 233 | CH₃ | H |  | —(CH₂)₄— |
| 234 | CH₃ | H |  | —(CH₂)₅— |
| 235 | CH₃ | H |  | —(CH₂)₂NH(CH₂)₂— |
| 236 | CH₃ | H |  | —(CH₂)₂NCH₃(CH₂)₂— |
| 237 | CH₃ | H |  | —(CH₂)₂O(CH₂)₂— |
| 238 | CH₃ | H |  | —CH₂CH=CHCH₂— |
| 239 | CH₃ | H |  | —CH₂CH=CHCH₂CH₂— |
| 240 | CH₃ | H |  | —CH=CHCH₂CH₂CH₂— |
| 241 | CH₃ | H | CH₃ | H |
| 242 | CH₃ | H | CH₃ | CH₃ |
| 243 | CH₃ | H | CH₃ | CH₂CH₃ |
| 244 | CH₃ | H | CH₃ | CH₂CH₂CH₃ |
| 245 | CH₃ | H | CH₃ | CH₂CH₂CH₂CH₃ |
| 246 | CH₃ | H | CH₃ | CH(CH₃)₂ |
| 247 | CH₃ | H | CH₃ | CH₂CH(CH₃)₂ |
| 248 | CH₃ | H | CH₃ | CH(CH₃)CH₂CH₃ |
| 249 | CH₃ | H | CH₃ | C(CH₃)₃ |
| 250 | CH₃ | H | CH₃ | CH₂OCH₃ |
| 251 | CH₃ | H | CH₃ | CH₂CH₂OCH₃ |
| 252 | CH₃ | H | CH₃ | CH₂OCH₂CH₃ |
| 253 | CH₃ | H | CH₃ | CH₂CH₂OCH₂CH₃ |
| 254 | CH₃ | H | CH₃ | CH(CH₃)CH₂OCH₃ |
| 255 | CH₃ | H | CH₃ | CH₂CH₂Cl |
| 256 | CH₃ | H | CH₃ | CH₂CH₂SCH₃ |
| 257 | CH₃ | H | CH₃ | CH₂CH₂S(O)CH₃ |
| 258 | CH₃ | H | CH₃ | CH₂CH₂S(O)₂CH₃ |
| 259 | CH₃ | H | CH₃ | CH₂CH₂CN |
| 260 | CH₃ | H | CH₃ | CH₂CH₂CO₂CH₃ |
| 261 | CH₃ | H | CH₃ | CH₂CH₂CO₂CH₂CH₃ |
| 262 | CH₃ | H | CH₃ | CH₂CH₂NH₂ |
| 263 | CH₃ | H | CH₃ | CH₂CH₂N(CH₃)₂ |
| 264 | CH₃ | H | CH₃ | CH₂CH₂N(CH₂CH₃)₂ |
| 265 | CH₃ | H | CH₃ | CH₂CH=CH₂ |
| 266 | CH₃ | H | CH₃ | C(CH₃)=CH₂ |
| 267 | CH₃ | H | CH₃ | CH₂CH=CHCH₃ |
| 268 | CH₃ | H | CH₃ | C(CH₃)CH=CHCH₃ |
| 269 | CH₃ | H | CH₃ | CH₂C≡CH |
| 270 | CH₃ | H | CH₃ | CH(CH₃)C≡CH |
| 271 | CH₃ | H | CH₃ | CH₂C≡CCH₃ |
| 272 | CH₃ | H | CH₃ | Ph |
| 273 | CH₃ | H | CH₂CH₃ | H |
| 274 | CH₃ | H | CH₂CH₃ | CH₃ |
| 275 | CH₃ | H | CH₂CH₃ | CH₂CH₃ |
| 276 | CH₃ | H | CH₂CH₃ | CH₂CH₂CH₃ |
| 277 | CH₃ | H | CH₂CH₃ | CH₂CH₂CH₂CH₃ |
| 278 | CH₃ | H | CH₂CH₃ | CH(CH₃)₂ |
| 279 | CH₃ | H | CH₂CH₃ | CH₂CH(CH₃)₂ |
| 280 | CH₃ | H | CH₂CH₃ | CH(CH₃)CH₂CH₃ |
| 281 | CH₃ | H | CH₂CH₃ | C(CH₃)₃ |
| 282 | CH₃ | H | CH₂CH₃ | CH₂OCH₃ |
| 283 | CH₃ | H | CH₂CH₃ | CH₂CH₂OCH₃ |
| 284 | CH₃ | H | CH₂CH₃ | CH₂OCH₂CH₃ |
| 285 | CH₃ | H | CH₂CH₃ | CH₂CH₂OCH₂CH₃ |
| 286 | CH₃ | H | CH₂CH₃ | CH(CH₃)CH₂OCH₃ |
| 287 | CH₃ | H | CH₂CH₃ | CH₂CH₂Cl |
| 288 | CH₃ | H | CH₂CH₃ | CH₂CH₂SCH₃ |
| 289 | CH₃ | H | CH₂CH₃ | CH₂CH₂S(O)CH₃ |
| 290 | CH₃ | H | CH₂CH₃ | CH₂CH₂S(O)₂CH₃ |
| 291 | CH₃ | H | CH₂CH₃ | CH₂CH₂CN |
| 292 | CH₃ | H | CH₂CH₃ | CH₂CH₂CO₂CH₃ |
| 293 | CH₃ | H | CH₂CH₃ | CH₂CH₂CO₂CH₂CH₃ |
| 294 | CH₃ | H | CH₂CH₃ | CH₂CH₂NH₂ |
| 295 | CH₃ | H | CH₂CH₃ | CH₂CH₂N(CH₃)₂ |
| 296 | CH₃ | H | CH₂CH₃ | CH₂CH₂N(CH₂CH₃)₂ |
| 297 | CH₃ | H | CH₂CH₃ | CH₂CH=CH₂ |
| 298 | CH₃ | H | CH₂CH₃ | C(CH₃)=CH₂ |
| 299 | CH₃ | H | CH₂CH₃ | CH₂CH=CHCH₃ |
| 300 | CH₃ | H | CH₂CH₃ | C(CH₃)CH=CHCH₃ |
| 301 | CH₃ | H | CH₂CH₃ | CH₂C≡CH |
| 302 | CH₃ | H | CH₂CH₃ | CH(CH₃)C≡CH |
| 303 | CH₃ | H | CH₂CH₃ | CH₂C≡CCH₃ |
| 304 | CH₃ | H | CH₂CH₃ | Ph |
| 305 | CH₃ | H | CH₂CH₂CH₃ | H |
| 306 | CH₃ | H | CH₂CH₂CH₃ | CH₃ |
| 307 | CH₃ | H | CH₂CH₂CH₃ | CH₂CH₃ |
| 308 | CH₃ | H | CH₂CH₂CH₃ | CH₂CH₂CH₃ |

TABLE 1-continued

| No. | R⁴ | R⁵ | R⁷ | R⁸ |
|---|---|---|---|---|
| 309 | CH₃ | H | CH₂CH₂CH₃ | CH₂CH₂CH₂CH₃ |
| 310 | CH₃ | H | CH₂CH₂CH₃ | CH(CH₃)₂ |
| 311 | CH₃ | H | CH₂CH₂CH₃ | CH₂CH(CH₃)₂ |
| 312 | CH₃ | H | CH₂CH₂CH₃ | CH(CH₃)CH₂CH₃ |
| 313 | CH₃ | H | CH₂CH₂CH₃ | C(CH₃)₃ |
| 314 | CH₃ | H | CH₂CH₂CH₃ | CH₂OCH₃ |
| 315 | CH₃ | H | CH₂CH₂CH₃ | CH₂CH₂OCH₃ |
| 316 | CH₃ | H | CH₂CH₂CH₃ | CH₂OCH₂CH₃ |
| 317 | CH₃ | H | CH₂CH₂CH₃ | CH₂CH₂OCH₂CH₃ |
| 318 | CH₃ | H | CH₂CH₂CH₃ | CH(CH₃)CH₂OCH₃ |
| 319 | CH₃ | H | CH₂CH₂CH₃ | CH₂CH₂Cl |
| 320 | CH₃ | H | CH₂CH₂CH₃ | CH₂CH₂SCH₃ |
| 321 | CH₃ | H | CH₂CH₂CH₃ | CH₂CH₂S(O)CH₃ |
| 322 | CH₃ | H | CH₂CH₂CH₃ | CH₂CH₂S(O)₂CH₃ |
| 323 | CH₃ | H | CH₂CH₂CH₃ | CH₂CH₂CN |
| 324 | CH₃ | H | CH₂CH₂CH₃ | CH₂CH₂CO₂CH₃ |
| 325 | CH₃ | H | CH₂CH₂CH₃ | CH₂CH₂CO₂CH₂CH₃ |
| 326 | CH₃ | H | CH₂CH₂CH₃ | CH₂CH₂NH₂ |
| 327 | CH₃ | H | CH₂CH₂CH₃ | CH₂CH₂N(CH₃)₂ |
| 328 | CH₃ | H | CH₂CH₂CH₃ | CH₂CH₂N(CH₂CH₃)₂ |
| 329 | CH₃ | H | CH₂CH₂CH₃ | CH₂CH=CH₂ |
| 330 | CH₃ | H | CH₂CH₂CH₃ | C(CH₃)=CH₂ |
| 331 | CH₃ | H | CH₂CH₂CH₃ | CH₂CH=CHCH₃ |
| 332 | CH₃ | H | CH₂CH₂CH₃ | C(CH₃)CH=CHCH₃ |
| 333 | CH₃ | H | CH₂CH₂CH₃ | CH₂C≡CH |
| 334 | CH₃ | H | CH₂CH₂CH₃ | CH(CH₃)C≡CH |
| 335 | CH₃ | H | CH₂CH₂CH₃ | CH₂C≡CHCH₃ |
| 336 | CH₃ | H | CH₂CH₂CH₃ | Ph |
| 337 | CH₃ | H | CH(CH₃)₂ | H |
| 338 | CH₃ | H | CH(CH₃)₂ | CH₃ |
| 339 | CH₃ | H | CH(CH₃)₂ | CH₂CH₃ |
| 340 | CH₃ | H | CH(CH₃)₂ | CH₂CH₂CH₃ |
| 341 | CH₃ | H | CH(CH₃)₂ | CH₂CH₂CH₂CH₃ |
| 342 | CH₃ | H | CH(CH₃)₂ | CH(CH₃)₂ |
| 343 | CH₃ | H | CH(CH₃)₂ | CH₂CH(CH₃)₂ |
| 344 | CH₃ | H | CH(CH₃)₂ | CH(CH₃)CH₂CH₃ |
| 345 | CH₃ | H | CH(CH₃)₂ | C(CH₃)₃ |
| 346 | CH₃ | H | CH(CH₃)₂ | CH₂OCH₃ |
| 347 | CH₃ | H | CH(CH₃)₂ | CH₂CH₂OCH₃ |
| 348 | CH₃ | H | CH(CH₃)₂ | CH₂OCH₂CH₃ |
| 349 | CH₃ | H | CH(CH₃)₂ | CH₂CH₂OCH₂CH₃ |
| 350 | CH₃ | H | CH(CH₃)₂ | CH(CH₃)CH₂OCH₃ |
| 351 | CH₃ | H | CH(CH₃)₂ | CH₂CH₂Cl |
| 352 | CH₃ | H | CH(CH₃)₂ | CH₂CH₂SCH₃ |
| 353 | CH₃ | H | CH(CH₃)₂ | CH₂CH₂S(O)CH₃ |
| 354 | CH₃ | H | CH(CH₃)₂ | CH₂CH₂S(O)₂CH₃ |
| 355 | CH₃ | H | CH(CH₃)₂ | CH₂CH₂CN |
| 356 | CH₃ | H | CH(CH₃)₂ | CH₂CH₂CO₂CH₃ |
| 357 | CH₃ | H | CH(CH₃)₂ | CH₂CH₂CO₂CH₂CH₃ |
| 358 | CH₃ | H | CH(CH₃)₂ | CH₂CH₂NH₂ |
| 359 | CH₃ | H | CH(CH₃)₂ | CH₂CH₂N(CH₃)₂ |
| 360 | CH₃ | H | CH(CH₃)₂ | CH₂CH₂N(CH₂CH₃)₂ |
| 361 | CH₃ | H | CH(CH₃)₂ | CH₂CH=CH₂ |
| 362 | CH₃ | H | CH(CH₃)₂ | C(CH₃)=CH₂ |
| 363 | CH₃ | H | CH(CH₃)₂ | CH₂CH=CHCH₃ |
| 364 | CH₃ | H | CH(CH₃)₂ | C(CH₃)CH=CHCH₃ |
| 365 | CH₃ | H | CH(CH₃)₂ | CH₂C≡CH |
| 366 | CH₃ | H | CH(CH₃)₂ | CH(CH₃)C≡CH |
| 367 | CH₃ | H | CH(CH₃)₂ | CH₂C≡CHCH₃ |
| 368 | CH₃ | H | CH(CH₃)₂ | Ph |
| 369 | CH₃ | H | CH₂CH=CH₂ | H |
| 370 | CH₃ | H | CH₂CH=CH₂ | CH₃ |
| 371 | CH₃ | H | CH₂CH=CH₂ | CH₂CH₃ |
| 372 | CH₃ | H | CH₂CH=CH₂ | CH₂CH₂CH₃ |
| 373 | CH₃ | H | CH₂CH=CH₂ | CH₂CH₂CH₂CH₃ |
| 374 | CH₃ | H | CH₂CH=CH₂ | CH(CH₃)₂ |
| 375 | CH₃ | H | CH₂CH=CH₂ | CH₂CH(CH₃)₂ |
| 376 | CH₃ | H | CH₂CH=CH₂ | CH(CH₃)CH₂CH₃ |
| 377 | CH₃ | H | CH₂CH=CH₂ | C(CH₃)₃ |
| 378 | CH₃ | H | CH₂CH=CH₂ | CH₂OCH₃ |
| 379 | CH₃ | H | CH₂CH=CH₂ | CH₂CH₂OCH₃ |
| 380 | CH₃ | H | CH₂CH=CH₂ | CH₂OCH₂CH₃ |
| 381 | CH₃ | H | CH₂CH=CH₂ | CH₂CH₂OCH₂CH₃ |
| 382 | CH₃ | H | CH₂CH=CH₂ | CH(CH₃)CH₂OCH₃ |
| 383 | CH₃ | H | CH₂CH=CH₂ | CH₂CH₂Cl |
| 384 | CH₃ | H | CH₂CH=CH₂ | CH₂CH₂SCH₃ |
| 385 | CH₃ | H | CH₂CH=CH₂ | CH₂CH₂S(O)CH₃ |
| 386 | CH₃ | H | CH₂CH=CH₂ | CH₂CH₂S(O)₂CH₃ |
| 387 | CH₃ | H | CH₂CH=CH₂ | CH₂CH₂CN |
| 388 | CH₃ | H | CH₂CH=CH₂ | CH₂CH₂CO₂CH₃ |
| 389 | CH₃ | H | CH₂CH=CH₂ | CH₂CH₂CO₂CH₂CH₃ |
| 390 | CH₃ | H | CH₂CH=CH₂ | CH₂CH₂NH₂ |
| 391 | CH₃ | H | CH₂CH=CH₂ | CH₂CH₂N(CH₃)₂ |
| 392 | CH₃ | H | CH₂CH=CH₂ | CH₂CH₂N(CH₂CH₃)₂ |
| 393 | CH₃ | H | CH₂CH=CH₂ | CH₂CH=CH₂ |
| 394 | CH₃ | H | CH₂CH=CH₂ | C(CH₃)=CH₂ |
| 395 | CH₃ | H | CH₂CH=CH₂ | CH₂CH=CHCH₃ |
| 396 | CH₃ | H | CH₂CH=CH₂ | C(CH₃)CH=CHCH₃ |
| 397 | CH₃ | H | CH₂CH=CH₂ | CH₂C≡CH |
| 398 | CH₃ | H | CH₂CH=CH₂ | CH(CH₃)C≡CH |
| 399 | CH₃ | H | CH₂CH=CH₂ | CH₂C≡CHCH₃ |
| 400 | CH₃ | H | CH₂CH=CH₂ | Ph |
| 401 | CH₃ | CH₃ | H | H |
| 402 | CH₃ | CH₃ | H | CH₃ |
| 403 | CH₃ | CH₃ | H | CH₂CH₃ |
| 404 | CH₃ | CH₃ | H | CH₂CH₂CH₃ |
| 405 | CH₃ | CH₃ | H | CH₂CH₂CH₂CH₃ |
| 406 | CH₃ | CH₃ | H | CH(CH₃)₂ |
| 407 | CH₃ | CH₃ | H | CH₂CH(CH₃)₂ |
| 408 | CH₃ | CH₃ | H | CH(CH₃)CH₂CH₃ |
| 409 | CH₃ | CH₃ | H | C(CH₃)₃ |
| 410 | CH₃ | CH₃ | H | CH₂OCH₃ |
| 411 | CH₃ | CH₃ | H | CH₂CH₂OCH₃ |
| 412 | CH₃ | CH₃ | H | CH₂OCH₂CH₃ |
| 413 | CH₃ | CH₃ | H | CH₂CH₂OCH₂CH₃ |
| 414 | CH₃ | CH₃ | H | CH(CH₃)CH₂OCH₃ |
| 415 | CH₃ | CH₃ | H | CH₂CH₂Cl |
| 416 | CH₃ | CH₃ | H | CH₂CH₂SCH₃ |
| 417 | CH₃ | CH₃ | H | CH₂CH₂S(O)CH₃ |
| 418 | CH₃ | CH₃ | H | CH₂CH₂S(O)₂CH₃ |
| 419 | CH₃ | CH₃ | H | CH₂CH₂CN |
| 420 | CH₃ | CH₃ | H | CH₂CH₂CO₂CH₃ |
| 421 | CH₃ | CH₃ | H | CH₂CH₂CO₂CH₂CH₃ |
| 422 | CH₃ | CH₃ | H | CH₂CH₂NH₂ |
| 423 | CH₃ | CH₃ | H | CH₂CH₂N(CH₃)₂ |
| 424 | CH₃ | CH₃ | H | CH₂CH₂N(CH₂CH₃)₂ |
| 425 | CH₃ | CH₃ | H | CH₂CH=CH₂ |
| 426 | CH₃ | CH₃ | H | C(CH₃)=CH₂ |
| 427 | CH₃ | CH₃ | H | CH₂CH=CHCH₃ |
| 428 | CH₃ | CH₃ | H | C(CH₃)CH=CHCH₃ |
| 429 | CH₃ | CH₃ | H | CH₂C≡CH |
| 430 | CH₃ | CH₃ | H | CH(CH₃)C≡CH |
| 431 | CH₃ | CH₃ | H | CH₂C≡CHCH₃ |
| 432 | CH₃ | CH₃ | H | Ph |
| 433 | CH₃ | CH₃ | | —(CH₂)₄— |
| 434 | CH₃ | CH₃ | | —(CH₂)₅— |
| 435 | CH₃ | CH₃ | | —(CH₂)₂NH(CH₂)₂— |
| 436 | CH₃ | CH₃ | | —(CH₂)₂NCH₃(CH₂)₂— |
| 437 | CH₃ | CH₃ | | —(CH₂)₂O(CH₂)₂— |
| 438 | CH₃ | CH₃ | | —CH₂CH=CHCH₂— |
| 439 | CH₃ | CH₃ | | —CH₂CH=CHCH₂CH₂— |
| 440 | CH₃ | CH₃ | | —CH=CHCH₂CH₂CH₂— |
| 441 | CH₃ | CH₃ | CH₃ | H |
| 442 | CH₃ | CH₃ | CH₃ | CH₃ |
| 443 | CH₃ | CH₃ | CH₃ | CH₂CH₃ |
| 444 | CH₃ | CH₃ | CH₃ | CH₂CH₂CH₃ |
| 445 | CH₃ | CH₃ | CH₃ | CH₂CH₂CH₂CH₃ |
| 446 | CH₃ | CH₃ | CH₃ | CH(CH₃)₂ |
| 447 | CH₃ | CH₃ | CH₃ | CH₂CH(CH₃)₂ |
| 448 | CH₃ | CH₃ | CH₃ | CH(CH₃)CH₂CH₃ |
| 449 | CH₃ | CH₃ | CH₃ | C(CH₃)₃ |
| 450 | CH₃ | CH₃ | CH₃ | CH₂OCH₃ |
| 451 | CH₃ | CH₃ | CH₃ | CH₂CH₂OCH₃ |
| 452 | CH₃ | CH₃ | CH₃ | CH₂OCH₂CH₃ |
| 453 | CH₃ | CH₃ | CH₃ | CH₂CH₂OCH₂CH₃ |
| 454 | CH₃ | CH₃ | CH₃ | CH(CH₃)CH₂OCH₃ |
| 455 | CH₃ | CH₃ | CH₃ | CH₂CH₂Cl |
| 456 | CH₃ | CH₃ | CH₃ | CH₂CH₂SCH₃ |
| 457 | CH₃ | CH₃ | CH₃ | CH₂CH₂S(O)CH₃ |
| 458 | CH₃ | CH₃ | CH₃ | CH₂CH₂S(O)₂CH₃ |
| 459 | CH₃ | CH₃ | CH₃ | CH₂CH₂CN |
| 460 | CH₃ | CH₃ | CH₃ | CH₂CH₂CO₂CH₃ |
| 461 | CH₃ | CH₃ | CH₃ | CH₂CH₂CO₂CH₂CH₃ |
| 462 | CH₃ | CH₃ | CH₃ | CH₂CH₂NH₂ |

TABLE 1-continued

| No. | $R^4$ | $R^5$ | $R^7$ | $R^8$ |
|---|---|---|---|---|
| 463 | $CH_3$ | $CH_3$ | $CH_3$ | $CH_2CH_2N(CH_3)_2$ |
| 464 | $CH_3$ | $CH_3$ | $CH_3$ | $CH_2CH_2N(CH_2CH_3)_2$ |
| 465 | $CH_3$ | $CH_3$ | $CH_3$ | $CH_2CH{=}CH_2$ |
| 466 | $CH_3$ | $CH_3$ | $CH_3$ | $C(CH_3){=}CH_2$ |
| 467 | $CH_3$ | $CH_3$ | $CH_3$ | $CH_2CH{=}CHCH_3$ |
| 468 | $CH_3$ | $CH_3$ | $CH_3$ | $C(CH_3)CH{=}CHCH_3$ |
| 469 | $CH_3$ | $CH_3$ | $CH_3$ | $CH_2C{\equiv}CH$ |
| 470 | $CH_3$ | $CH_3$ | $CH_3$ | $CH(CH_3)C{\equiv}CH$ |
| 471 | $CH_3$ | $CH_3$ | $CH_3$ | $CH_2C{\equiv}CHCH_3$ |
| 472 | $CH_3$ | $CH_3$ | $CH_3$ | Ph |
| 473 | $CH_3$ | $CH_3$ | $CH_2CH_3$ | H |
| 474 | $CH_3$ | $CH_3$ | $CH_2CH_3$ | $CH_3$ |
| 475 | $CH_3$ | $CH_3$ | $CH_2CH_3$ | $CH_2CH_3$ |
| 476 | $CH_3$ | $CH_3$ | $CH_2CH_3$ | $CH_2CH_2CH_3$ |
| 477 | $CH_3$ | $CH_3$ | $CH_2CH_3$ | $CH_2CH_2CH_2CH_3$ |
| 478 | $CH_3$ | $CH_3$ | $CH_2CH_3$ | $CH(CH_3)_2$ |
| 479 | $CH_3$ | $CH_3$ | $CH_2CH_3$ | $CH_2CH(CH_3)_2$ |
| 480 | $CH_3$ | $CH_3$ | $CH_2CH_3$ | $CH(CH_3)CH_2CH_3$ |
| 481 | $CH_3$ | $CH_3$ | $CH_2CH_3$ | $C(CH_3)_3$ |
| 482 | $CH_3$ | $CH_3$ | $CH_2CH_3$ | $CH_2OCH_3$ |
| 483 | $CH_3$ | $CH_3$ | $CH_2CH_3$ | $CH_2CH_2OCH_3$ |
| 484 | $CH_3$ | $CH_3$ | $CH_2CH_3$ | $CH_2OCH_2CH_3$ |
| 485 | $CH_3$ | $CH_3$ | $CH_2CH_3$ | $CH_2CH_2OCH_2CH_3$ |
| 486 | $CH_3$ | $CH_3$ | $CH_2CH_3$ | $CH(CH_3)CH_2OCH_3$ |
| 487 | $CH_3$ | $CH_3$ | $CH_2CH_3$ | $CH_2CH_2Cl$ |
| 488 | $CH_3$ | $CH_3$ | $CH_2CH_3$ | $CH_2CH_2SCH_3$ |
| 489 | $CH_3$ | $CH_3$ | $CH_2CH_3$ | $CH_2CH_2S(O)CH_3$ |
| 490 | $CH_3$ | $CH_3$ | $CH_2CH_3$ | $CH_2CH_2S(O)_2CH_3$ |
| 491 | $CH_3$ | $CH_3$ | $CH_2CH_3$ | $CH_2CH_2CN$ |
| 492 | $CH_3$ | $CH_3$ | $CH_2CH_3$ | $CH_2CH_2CO_2CH_3$ |
| 493 | $CH_3$ | $CH_3$ | $CH_2CH_3$ | $CH_2CH_2CO_2CH_2CH_3$ |
| 494 | $CH_3$ | $CH_3$ | $CH_2CH_3$ | $CH_2CH_2NH_2$ |
| 495 | $CH_3$ | $CH_3$ | $CH_2CH_3$ | $CH_2CH_2N(CH_3)_2$ |
| 496 | $CH_3$ | $CH_3$ | $CH_2CH_3$ | $CH_2CH_2N(CH_2CH_3)_2$ |
| 497 | $CH_3$ | $CH_3$ | $CH_2CH_3$ | $CH_2CH{=}CH_2$ |
| 498 | $CH_3$ | $CH_3$ | $CH_2CH_3$ | $C(CH_3){=}CH_2$ |
| 499 | $CH_3$ | $CH_3$ | $CH_2CH_3$ | $CH_2CH{=}CHCH_3$ |
| 500 | $CH_3$ | $CH_3$ | $CH_2CH_3$ | $C(CH_3)CH{=}CHCH_3$ |
| 501 | $CH_3$ | $CH_3$ | $CH_2CH_3$ | $CH_2C{\equiv}CH$ |
| 502 | $CH_3$ | $CH_3$ | $CH_2CH_3$ | $CH(CH_3)C{\equiv}CH$ |
| 503 | $CH_3$ | $CH_3$ | $CH_2CH_3$ | $CH_2C{\equiv}CHCH_3$ |
| 504 | $CH_3$ | $CH_3$ | $CH_2CH_3$ | Ph |
| 505 | $CH_3$ | $CH_3$ | $CH_2CH_2CH_3$ | H |
| 506 | $CH_3$ | $CH_3$ | $CH_2CH_2CH_3$ | $CH_3$ |
| 507 | $CH_3$ | $CH_3$ | $CH_2CH_2CH_3$ | $CH_2CH_3$ |
| 508 | $CH_3$ | $CH_3$ | $CH_2CH_2CH_3$ | $CH_2CH_2CH_3$ |
| 509 | $CH_3$ | $CH_3$ | $CH_2CH_2CH_3$ | $CH_2CH_2CH_2CH_3$ |
| 510 | $CH_3$ | $CH_3$ | $CH_2CH_2CH_3$ | $CH(CH_3)_2$ |
| 511 | $CH_3$ | $CH_3$ | $CH_2CH_2CH_3$ | $CH_2CH(CH_3)_2$ |
| 512 | $CH_3$ | $CH_3$ | $CH_2CH_2CH_3$ | $CH(CH_3)CH_2CH_3$ |
| 513 | $CH_3$ | $CH_3$ | $CH_2CH_2CH_3$ | $C(CH_3)_3$ |
| 514 | $CH_3$ | $CH_3$ | $CH_2CH_2CH_3$ | $CH_2OCH_3$ |
| 515 | $CH_3$ | $CH_3$ | $CH_2CH_2CH_3$ | $CH_2CH_2OCH_3$ |
| 516 | $CH_3$ | $CH_3$ | $CH_2CH_2CH_3$ | $CH_2OCH_2CH_3$ |
| 517 | $CH_3$ | $CH_3$ | $CH_2CH_2CH_3$ | $CH_2CH_2OCH_2CH_3$ |
| 518 | $CH_3$ | $CH_3$ | $CH_2CH_2CH_3$ | $CH(CH_3)CH_2OCH_3$ |
| 519 | $CH_3$ | $CH_3$ | $CH_2CH_2CH_3$ | $CH_2CH_2Cl$ |
| 520 | $CH_3$ | $CH_3$ | $CH_2CH_2CH_3$ | $CH_2CH_2SCH_3$ |
| 521 | $CH_3$ | $CH_3$ | $CH_2CH_2CH_3$ | $CH_2CH_2S(O)CH_3$ |
| 522 | $CH_3$ | $CH_3$ | $CH_2CH_2CH_3$ | $CH_2CH_2S(O)_2CH_3$ |
| 523 | $CH_3$ | $CH_3$ | $CH_2CH_2CH_3$ | $CH_2CH_2CN$ |
| 524 | $CH_3$ | $CH_3$ | $CH_2CH_2CH_3$ | $CH_2CH_2CO_2CH_3$ |
| 525 | $CH_3$ | $CH_3$ | $CH_2CH_2CH_3$ | $CH_2CH_2CO_2CH_2CH_3$ |
| 526 | $CH_3$ | $CH_3$ | $CH_2CH_2CH_3$ | $CH_2CH_2NH_2$ |
| 527 | $CH_3$ | $CH_3$ | $CH_2CH_2CH_3$ | $CH_2CH_2N(CH_3)_2$ |
| 528 | $CH_3$ | $CH_3$ | $CH_2CH_2CH_3$ | $CH_2CH_2N(CH_2CH_3)_2$ |
| 529 | $CH_3$ | $CH_3$ | $CH_2CH_2CH_3$ | $CH_2CH{=}CH_2$ |
| 530 | $CH_3$ | $CH_3$ | $CH_2CH_2CH_3$ | $C(CH_3){=}CH_2$ |
| 531 | $CH_3$ | $CH_3$ | $CH_2CH_2CH_3$ | $CH_2CH{=}CHCH_3$ |
| 532 | $CH_3$ | $CH_3$ | $CH_2CH_2CH_3$ | $C(CH_3)CH{=}CHCH_3$ |
| 533 | $CH_3$ | $CH_3$ | $CH_2CH_2CH_3$ | $CH_2C{\equiv}CH$ |
| 534 | $CH_3$ | $CH_3$ | $CH_2CH_2CH_3$ | $CH(CH_3)C{\equiv}CH$ |
| 535 | $CH_3$ | $CH_3$ | $CH_2CH_2CH_3$ | $CH_2C{\equiv}CHCH_3$ |
| 536 | $CH_3$ | $CH_3$ | $CH_2CH_2CH_3$ | Ph |
| 537 | $CH_3$ | $CH_3$ | $CH(CH_3)_2$ | H |
| 538 | $CH_3$ | $CH_3$ | $CH(CH_3)_2$ | $CH_3$ |
| 539 | $CH_3$ | $CH_3$ | $CH(CH_3)_2$ | $CH_2CH_3$ |
| 540 | $CH_3$ | $CH_3$ | $CH(CH_3)_2$ | $CH_2CH_2CH_3$ |
| 541 | $CH_3$ | $CH_3$ | $CH(CH_3)_2$ | $CH_2CH_2CH_2CH_3$ |
| 542 | $CH_3$ | $CH_3$ | $CH(CH_3)_2$ | $CH(CH_3)_2$ |
| 543 | $CH_3$ | $CH_3$ | $CH(CH_3)_2$ | $CH_2CH(CH_3)_2$ |
| 544 | $CH_3$ | $CH_3$ | $CH(CH_3)_2$ | $CH(CH_3)CH_2CH_3$ |
| 545 | $CH_3$ | $CH_3$ | $CH(CH_3)_2$ | $C(CH_3)_3$ |
| 546 | $CH_3$ | $CH_3$ | $CH(CH_3)_2$ | $CH_2OCH_3$ |
| 547 | $CH_3$ | $CH_3$ | $CH(CH_3)_2$ | $CH_2CH_2OCH_3$ |
| 548 | $CH_3$ | $CH_3$ | $CH(CH_3)_2$ | $CH_2OCH_2CH_3$ |
| 549 | $CH_3$ | $CH_3$ | $CH(CH_3)_2$ | $CH_2CH_2OCH_2CH_3$ |
| 550 | $CH_3$ | $CH_3$ | $CH(CH_3)_2$ | $CH(CH_3)CH_2OCH_3$ |
| 551 | $CH_3$ | $CH_3$ | $CH(CH_3)_2$ | $CH_2CH_2Cl$ |
| 552 | $CH_3$ | $CH_3$ | $CH(CH_3)_2$ | $CH_2CH_2SCH_3$ |
| 553 | $CH_3$ | $CH_3$ | $CH(CH_3)_2$ | $CH_2CH_2S(O)CH_3$ |
| 554 | $CH_3$ | $CH_3$ | $CH(CH_3)_2$ | $CH_2CH_2S(O)_2CH_3$ |
| 555 | $CH_3$ | $CH_3$ | $CH(CH_3)_2$ | $CH_2CH_2CN$ |
| 556 | $CH_3$ | $CH_3$ | $CH(CH_3)_2$ | $CH_2CH_2CO_2CH_3$ |
| 557 | $CH_3$ | $CH_3$ | $CH(CH_3)_2$ | $CH_2CH_2CO_2CH_2CH_3$ |
| 558 | $CH_3$ | $CH_3$ | $CH(CH_3)_2$ | $CH_2CH_2NH_2$ |
| 559 | $CH_3$ | $CH_3$ | $CH(CH_3)_2$ | $CH_2CH_2N(CH_3)_2$ |
| 560 | $CH_3$ | $CH_3$ | $CH(CH_3)_2$ | $CH_2CH_2N(CH_2CH_3)_2$ |
| 561 | $CH_3$ | $CH_3$ | $CH(CH_3)_2$ | $CH_2CH{=}CH_2$ |
| 562 | $CH_3$ | $CH_3$ | $CH(CH_3)_2$ | $C(CH_3){=}CH_2$ |
| 563 | $CH_3$ | $CH_3$ | $CH(CH_3)_2$ | $CH_2CH{=}CHCH_3$ |
| 564 | $CH_3$ | $CH_3$ | $CH(CH_3)_2$ | $C(CH_3)CH{=}CHCH_3$ |
| 565 | $CH_3$ | $CH_3$ | $CH(CH_3)_2$ | $CH_2C{\equiv}CH$ |
| 566 | $CH_3$ | $CH_3$ | $CH(CH_3)_2$ | $CH(CH_3)C{\equiv}CH$ |
| 567 | $CH_3$ | $CH_3$ | $CH(CH_3)_2$ | $CH_2C{\equiv}CHCH_3$ |
| 568 | $CH_3$ | $CH_3$ | $CH(CH_3)_2$ | Ph |
| 569 | $CH_3$ | $CH_3$ | $CH_2CH{=}CH_2$ | H |
| 570 | $CH_3$ | $CH_3$ | $CH_2CH{=}CH_2$ | $CH_3$ |
| 571 | $CH_3$ | $CH_3$ | $CH_2CH{=}CH_2$ | $CH_2CH_3$ |
| 572 | $CH_3$ | $CH_3$ | $CH_2CH{=}CH_2$ | $CH_2CH_2CH_3$ |
| 573 | $CH_3$ | $CH_3$ | $CH_2CH{=}CH_2$ | $CH_2CH_2CH_2CH_3$ |
| 574 | $CH_3$ | $CH_3$ | $CH_2CH{=}CH_2$ | $CH(CH_3)_2$ |
| 575 | $CH_3$ | $CH_3$ | $CH_2CH{=}CH_2$ | $CH_2CH(CH_3)_2$ |
| 576 | $CH_3$ | $CH_3$ | $CH_2CH{=}CH_2$ | $CH(CH_3)CH_2CH_3$ |
| 577 | $CH_3$ | $CH_3$ | $CH_2CH{=}CH_2$ | $C(CH_3)_3$ |
| 578 | $CH_3$ | $CH_3$ | $CH_2CH{=}CH_2$ | $CH_2OCH_3$ |
| 579 | $CH_3$ | $CH_3$ | $CH_2CH{=}CH_2$ | $CH_2CH_2OCH_3$ |
| 580 | $CH_3$ | $CH_3$ | $CH_2CH{=}CH_2$ | $CH_2OCH_2CH_3$ |
| 581 | $CH_3$ | $CH_3$ | $CH_2CH{=}CH_2$ | $CH_2CH_2OCH_2CH_3$ |
| 582 | $CH_3$ | $CH_3$ | $CH_2CH{=}CH_2$ | $CH(CH_3)CH_2OCH_3$ |
| 583 | $CH_3$ | $CH_3$ | $CH_2CH{=}CH_2$ | $CH_2CH_2Cl$ |
| 584 | $CH_3$ | $CH_3$ | $CH_2CH{=}CH_2$ | $CH_2CH_2SCH_3$ |
| 585 | $CH_3$ | $CH_3$ | $CH_2CH{=}CH_2$ | $CH_2CH_2S(O)CH_3$ |
| 586 | $CH_3$ | $CH_3$ | $CH_2CH{=}CH_2$ | $CH_2CH_2S(O)_2CH_3$ |
| 587 | $CH_3$ | $CH_3$ | $CH_2CH{=}CH_2$ | $CH_2CH_2CN$ |
| 588 | $CH_3$ | $CH_3$ | $CH_2CH{=}CH_2$ | $CH_2CH_2CO_2CH_3$ |
| 589 | $CH_3$ | $CH_3$ | $CH_2CH{=}CH_2$ | $CH_2CH_2CO_2CH_2CH_3$ |
| 590 | $CH_3$ | $CH_3$ | $CH_2CH{=}CH_2$ | $CH_2CH_2NH_2$ |
| 591 | $CH_3$ | $CH_3$ | $CH_2CH{=}CH_2$ | $CH_2CH_2N(CH_3)_2$ |
| 592 | $CH_3$ | $CH_3$ | $CH_2CH{=}CH_2$ | $CH_2CH_2N(CH_2CH_3)_2$ |
| 593 | $CH_3$ | $CH_3$ | $CH_2CH{=}CH_2$ | $CH_2CH{=}CH_2$ |
| 594 | $CH_3$ | $CH_3$ | $CH_2CH{=}CH_2$ | $C(CH_3){=}CH_2$ |
| 595 | $CH_3$ | $CH_3$ | $CH_2CH{=}CH_2$ | $CH_2CH{=}CHCH_3$ |
| 596 | $CH_3$ | $CH_3$ | $CH_2CH{=}CH_2$ | $C(CH_3)CH{=}CHCH_3$ |
| 597 | $CH_3$ | $CH_3$ | $CH_2CH{=}CH_2$ | $CH_2C{\equiv}CH$ |
| 598 | $CH_3$ | $CH_3$ | $CH_2CH{=}CH_2$ | $CH(CH_3)C{\equiv}CH$ |
| 599 | $CH_3$ | $CH_3$ | $CH_2CH{=}CH_2$ | $CH_2C{\equiv}CHCH_3$ |
| 600 | $CH_3$ | $CH_3$ | $CH_2CH{=}CH_2$ | Ph |

Very particular preference is also given to the 3-heterocyclyl-substituted benzoic acid derivatives of the formula I-Ab (=I where $R^1$=II-A, $R^{10}$=methyl, $R^{11}$=trifluoromethyl and $R^{12}$=hydrogen, $R^2$=H, $R^3$=Cl, $R^6$=H, X=O), where $R^4$, $R^5$, $R^7$ and $R^8$ have the meanings mentioned above, in particular the meanings mentioned as being preferred. Examples of such compounds are the compounds I-Ab.1 to I-Ab.600 in which the variables $R^4$, $R^5$, $R^7$ and $R^8$ together have the meanings given in one row of Table 1.

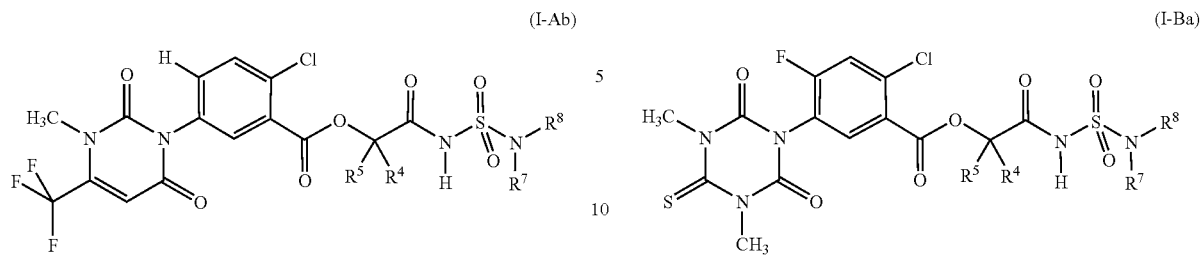

Very particular preference is also given to the 3-heterocyclyl-substituted benzoic acid derivatives of the formula I-Ac (≡I where $R^1$=II-A, $R^{10}$=amino, $R^{11}$=trifluoromethyl and $R^{12}$=hydrogen, $R^2$=F, $R^3$=Cl, $R^6$=H, X=O), where $R^4$, $R^5$, $R^7$ and $R^8$ have the meanings mentioned above, in particular the meanings mentioned as being preferred. Examples of such compounds are the compounds I-Ac.1 to I-Ac.600 in which the variables $R^4$, $R^5$, $R^7$ and $R^8$ together have the meanings given in one row of Table 1.

Among the compounds I-B preference is given to the 3-heterocyclyl-substituted benzoic acid derivatives of the formula I-Bb (≡I where $R^1$=II-B, $R^{13'}$, $R^{13}$ are each methyl, $R^2$=H, $R^3$=Cl; $R^6$=H, X=O) in which $R^4$, $R^5$, $R^7$ and $R^8$ have the meanings mentioned above, in particular the meanings mentioned as being preferred. Examples of such compounds are the compounds I-Bb.1 to I-Bb.600 in which the variables $R^4$, $R^5$, $R^7$ and $R^8$ together have the meanings given in one row of Table 1.

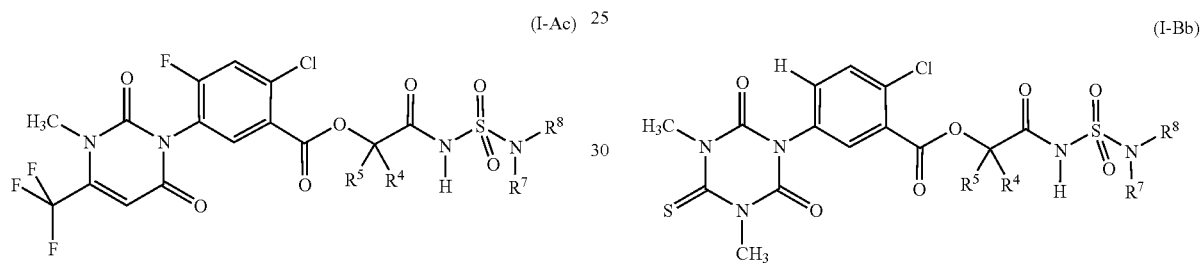

Very particular preference is also given to the 3-heterocyclyl-substituted benzoic acid derivatives of the formula I-Ad (≡I where $R^1$=II-A, $R^{10}$=amino, $R^{11}$=trifluoromethyl and $R^{12}$=hydrogen, $R^2$=H, $R^3$=Cl, $R^6$=H, X=O), where $R^4$, $R^5$, $R^7$ and $R^8$ have the meanings mentioned above, in particular the meanings mentioned as being preferred. Examples of such compounds are the compounds I-Ad.1 to I-Ad.600, in which the variables $R^4$, $R^5$, $R^7$ and $R^8$ together have the meanings given in one row of Table 1.

Among the compounds I-C preference is given to the 3-heterocyclyl-substituted benzoic acid derivatives of the formula I-Ca (≡I where $R^1$=II-C, $R^{14}$=chlorine, $R^{15}$, $R^{17}$=hydrogen, $R^{16}$=trifluoromethyl, $R^2$=F; $R^3$=Cl; $R^6$=H, X=O) in which $R^4$, $R^5$, $R^7$ and $R^8$ have the meanings mentioned above, in particular the meanings mentioned as being preferred. Examples of such compounds are the compounds I-Ca.1 to I-Ca.600 in which the variables $R^4$, $R^5$, $R^7$ and $R^8$ together have the meanings given in one row of Table 1.

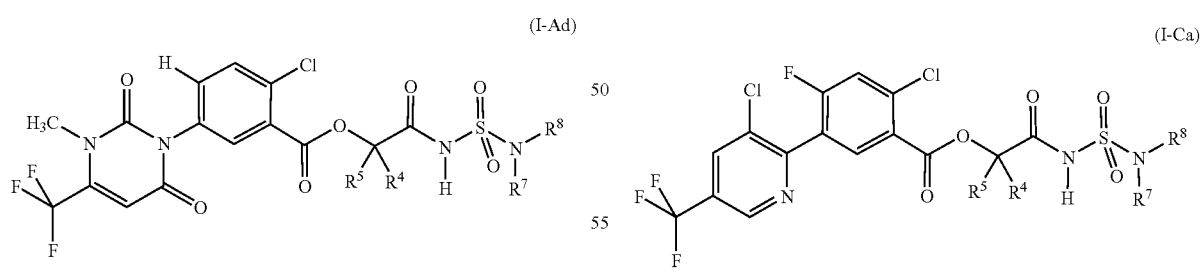

Among the compounds I-B preference is given to the 3-heterocyclyl-substituted benzoic acid derivatives of the formula I-Ba (≡I where $R^1$=II-B, $R^{13'}$, $R^{13}$ are each methyl, $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Ba.1 to I-Ba.600 in which the variables $R^4$, $R^5$, $R^7$ and $R^8$ together have the meanings given in one row of Table 1.

Among the compounds I-C preference is given to the 3-heterocyclyl-substituted benzoic acid derivatives of the formula I-Cb (≡I where $R^1$=II-C, $R^{14}$=chlorine, $R^{15}$, $R^{17}$=hydrogen, $R^{16}$=trifluoromethyl, $R^2$=H; $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Cb.1 to I-Cb.600 in which the variables $R^4$, $R^5$, $R^7$ and $R^8$ together have the meanings given in one row of Table 1.

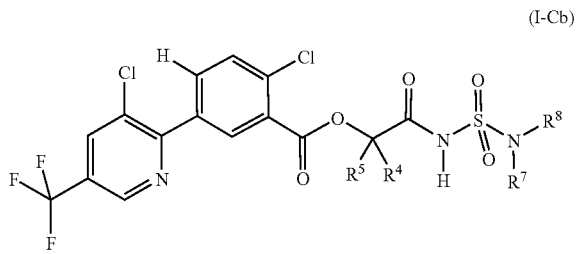

(I-Cb)

Among the compounds I-C preference is given to the 3-heterocyclyl-substituted benzoic acid derivatives of the formula I-Cc (=I where $R^1$=II-C, $R^{14}$=chlorine, $R^{15}$, $R^{17}$=hydrogen, $R^{16}$=methylsulfonyl, $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Cc.1 to I-Cc.600 in which the variables $R^4$, $R^5$, $R^7$ and $R^8$ together have the meanings given in one row of Table 1.

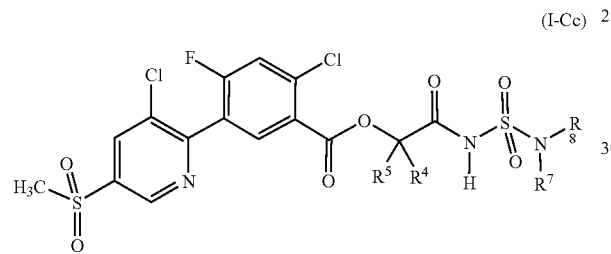

(I-Cc)

Among the compounds I-C preference is given to the 3-heterocyclyl-substituted benzoic acid derivatives of the formula I-Cd (=I where $R^1$=II-C, $R^{14}$=chlorine, $R^{15}$, $R^{17}$=hydrogen, $R^{16}$=methylsulfonyl; $R^2$=H, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Cd.1 to I-Cd.600 in which the variables $R^4$, $R^5$, $R^7$ and $R^8$ together have the meanings given in one row of Table 1.

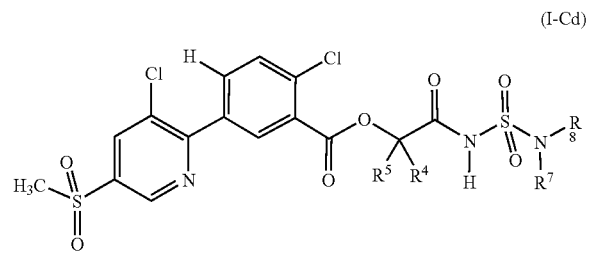

(I-Cd)

Among the compounds I-C preference is given to the 3-heterocyclyl-substituted benzoic acid derivatives of the formula I-Ce (=I where $R^1$=II-C, $R^{14}$=chlorine, $R^{15}$, $R^{17}$=hydrogen, $R^{16}$=methylsulfonyloxy, $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Ce.1 to I-Ce.600 in which the variables $R^4$, $R^5$, $R^7$ and $R^8$ together have the meanings given in one row of Table 1.

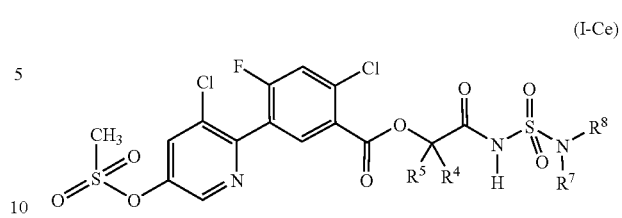

(I-Ce)

Among the compounds I-C preference is given to the 3-heterocyclyl-substituted benzoic acid derivatives of the formula I-Cf (=I where $R^1$=II-C, $R^{14}$=chlorine, $R^{15}$, $R^{17}$=hydrogen, $R^{16}$=methylsulfonyloxy, $R^2$=H, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Cf.1 to I-Cf.600 in which the variables $R^4$, $R^5$, $R^7$ and $R^8$ together have the meanings given in one row of Table 1.

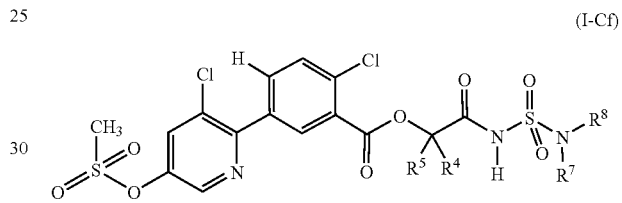

(I-Cf)

Among the compounds I-D preference is given to the 3-heterocyclyl-substituted benzoic acid derivatives of the formula I-Da (=I where $R^1$=II-D, $R^{18}$, $R^{20}$=hydrogen, $R^{19}$=trifluoromethyl, $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Da.1 to I-Da.600 in which the variables $R^4$, $R^5$, $R^7$ and $R^8$ together have the meanings given in one row of Table 1.

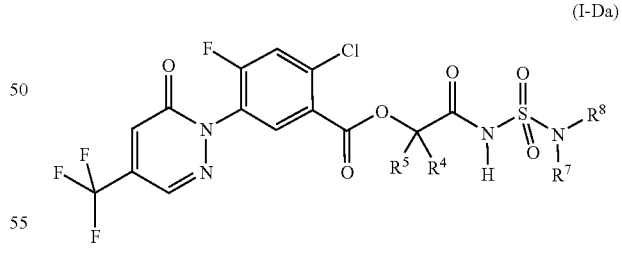

(I-Da)

Among the compounds I-D preference is given to the 3-heterocyclyl-substituted benzoic acid derivatives of the formula I-Db (=I where $R^1$=II-D, $R^{18}$, $R^{20}$=hydrogen, $R^{19}$=trifluoromethyl, $R^2$=H, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Db.1 to I-Db.600 in which the variables $R^4$, $R^5$, $R^7$ and $R^8$ together have the meanings given in one row of Table 1.

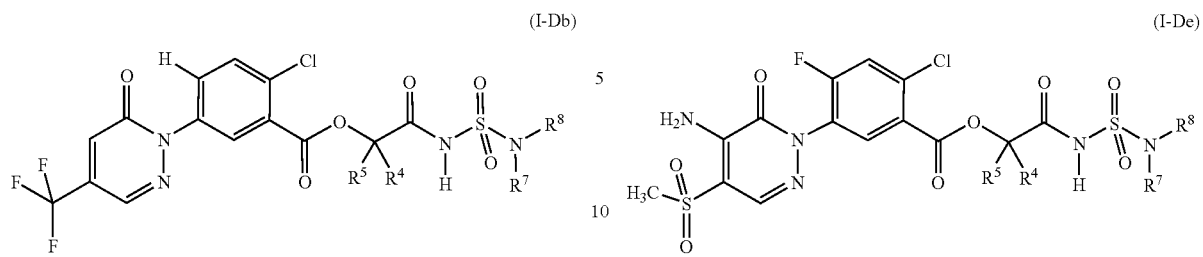

(I-Db)

(I-De)

Among the compounds I-D preference is given to the 3-heterocyclyl-substituted benzoic acid derivatives of the formula I-Dc (≡I where $R^1$=II-D, $R^{18}$=methyl, $R^{19}$=trifluoromethyl, $R^{20}$=hydrogen, $R^2$=F, $R^3$=Cl; $R^6$=H, X=O) in which $R^4$, $R^5$, $R^7$ and $R^8$ have the meanings mentioned above, in particular the meanings mentioned as being preferred. Examples of such compounds are the compounds I-Dc.1 to I-Dc.600 in which the variables $R^4$, $R^5$, $R^7$ and $R^8$ together have the meanings given in one row of Table 1.

Among the compounds I-D preference is given to the 3-heterocyclyl-substituted benzoic acid derivatives of the formula I-Df (≡I where $R^1$=II-D, $R^{18}$=amino, $R^{19}$=methylsulfonyl, $R^{20}$=hydrogen, $R^2$=H, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Df.1 to I-Df.600 in which the variables $R^4$, $R^5$, $R^7$ and $R^8$ together have the meanings given in one row of Table 1.

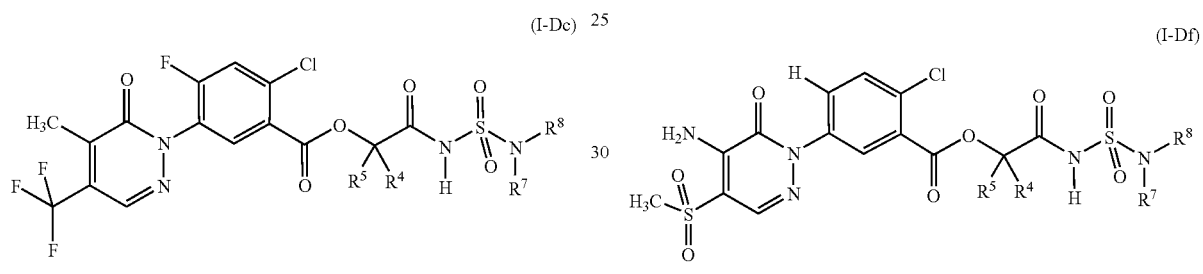

(I-Dc)

(I-Df)

Among the compounds I-D preference is given to the 3-heterocyclyl-substituted benzoic acid derivatives of the formula I-Dd (≡I where $R^1$=II-D, $R^{18}$=methyl, $R^{19}$=trifluoromethyl, $R^{20}$=hydrogen; $R^2$=H, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Dd.1 to I-Dd.600 in which the variables $R^4$, $R^5$, $R^7$ and $R^8$ together have the meanings given in one row of Table 1.

Among the compounds I-E preference is given to the 3-heterocyclyl-substituted benzoic acid derivatives of the formula I-Ea (≡I where $R^1$=II-E, $R^{21}$=chlorine, $R^{22}$=trifluoromethyl, $R^{23}$=methyl, $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Ea.1 to I-Ea.600 in which the variables $R^4$, $R^5$, $R^7$ and $R^8$ together have the meanings given in one row of Table 1.

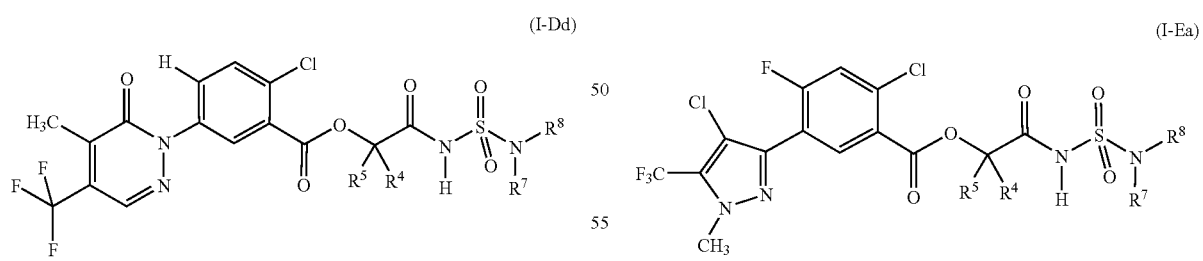

(I-Dd)

(I-Ea)

Among the compounds I-D preference is given to the 3-heterocyclyl-substituted benzoic acid derivatives of the formula I-De (≡I where $R^1$=II-D, $R^{18}$=amino, $R^{19}$=methylsulfonyl, $R^{20}$=hydrogen; $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-De.1 to I-De.600 in which the variables $R^4$, $R^5$, $R^7$ and $R^8$ together have the meanings given in one row of Table 1.

Among the compounds I-E preference is given to the 3-heterocyclyl-substituted benzoic acid derivatives of the formula I-Eb (≡I where $R^1$=II-E, $R^{21}$=bromine, $R^{22}$=trifluoromethyl, $R^{23}$=methyl, $R^2$=Cl, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Eb.1 to I-Eb.600 in which the variables $R^4$, $R^5$, $R^7$ and $R^8$ together have the meanings given in one row of Table 1.

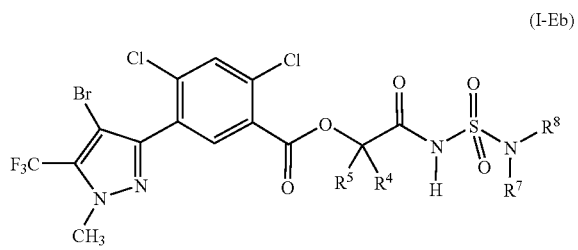

(I-Eb)

Among the compounds I-E preference is given to the 3-heterocyclyl-substituted benzoic acid derivatives of the formula I-Ec (≡I where $R^1$=II-E, $R^{21}$=chlorine, $R^{22}$=trifluoromethyl, $R^{23}$=methyl; $R^2$=H, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Ec.1 to I-Ec.600 in which the variables $R^4$, $R^5$, $R^7$ and $R^8$ together have the meanings given in one row of Table 1.

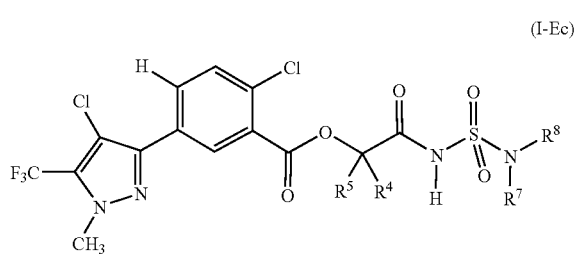

(I-Ec)

Among the compounds I-E preference is given to the 3-heterocyclyl-substituted benzoic acid derivatives of the formula I-Ed (≡I where $R^1$=II-E, $R^{21}$=chlorine, $R^{22}$=difluoromethoxy, $R^{23}$=methyl, $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Ed.1 to I-Ed.600 in which the variables $R^4$, $R^5$, $R^7$ and $R^8$ together have the meanings given in one row of Table 1.

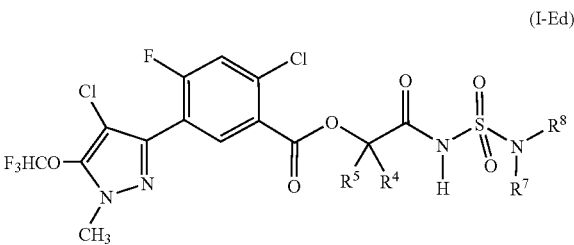

(I-Ed)

Among the compounds I-E preference is given to the 3-heterocyclyl-substituted benzoic acid derivatives of the formula I-Ee (≡I where $R^1$=II-E, $R^{21}$=chlorine, $R^{22}$=difluoromethoxy, $R^{23}$=methyl, $R^2$=H, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Ee.1 to I-Ee.600 in which the variables $R^4$, $R^5$, $R^7$ and $R^8$ together have the meanings given in one row of Table 1.

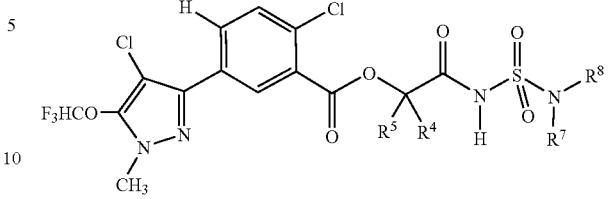

(I-Ee)

Among the compounds I-E preference is given to the 3-heterocyclyl-substituted benzoic acid derivatives of the formula I-Ef (≡I where $R^1$=II-E, $R^{21}$=bromine, $R^{22}$=difluoromethoxy, $R^{23}$=methyl, $R^2$=Cl, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Ef.1 to I-Ef.600 in which the variables $R^4$, $R^5$, $R^7$ and $R^8$ together have the meanings given in one row of Table 1.

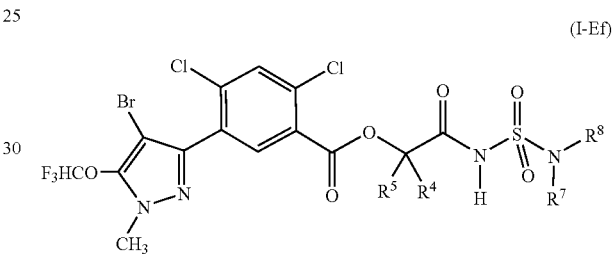

(I-Ef)

Among the compounds I-E preference is given to the 3-heterocyclyl-substituted benzoic acid derivatives of the formula I-Eg (≡I where $R^1$=II-E, $R^{21}$=chlorine, $R^{22}$=methylsulfonyl, $R^{23}$=methyl; $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Eg.1 to I-Eg.600 in which the variables $R^4$, $R^5$, $R^7$ and $R^8$ together have the meanings given in one row of Table 1.

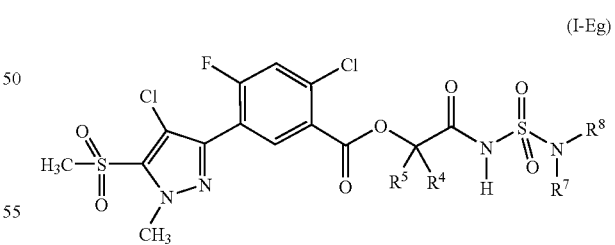

(I-Eg)

Among the compounds I-E preference is given to the 3-heterocyclyl-substituted benzoic acid derivatives of the formula I-Eh (≡I where $R^1$=II-E, $R^{21}$=bromine, $R^{22}$=methylsulfonyl, $R^{23}$=methyl, $R^2$=Cl, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Eh.1 to I-Eh.600 in which the variables $R^4$, $R^5$, $R^7$ and $R^8$ together have the meanings given in one row of Table 1.

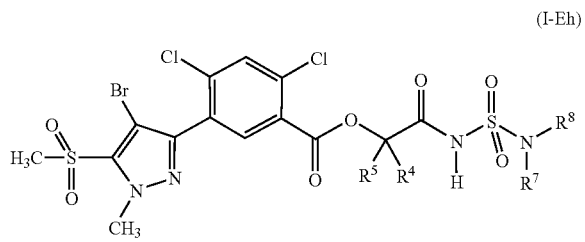
(I-Eh)

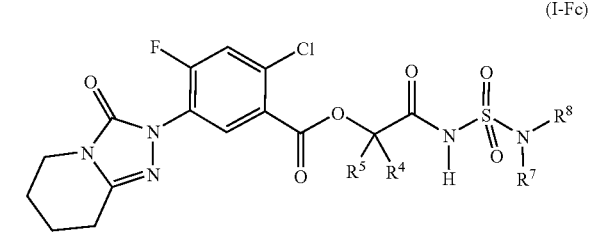
(I-Fc)

Among the compounds I-F preference is given to the 3-heterocyclyl-substituted benzoic acid derivatives of the formula I-Fb (≡I where $R^1$=II-F, $R^{24}$=difluoromethyl, $R^{25}$=methyl, $R^2$=Cl, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Fb.1 to I-Fb.600 in which the variables $R^4$ $R^5$, $R^7$ and $R^8$ together have the meanings given in one row of Table 1.

Among the compounds I-F preference is given to the 3-heterocyclyl-substituted benzoic acid derivatives of the formula I-Fd (≡I where $R^1$=II-F, $R^{24}$, $R^{25}$=(CH$_2$)$_4$, $R^2$=Cl, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Fd.1 to I-Fd.600 in which the variables $R^4$, $R^5$, $R^7$ and $R^8$ together have the meanings given in one row of Table 1.

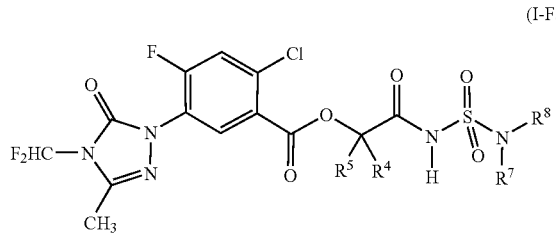
(I-Fa)

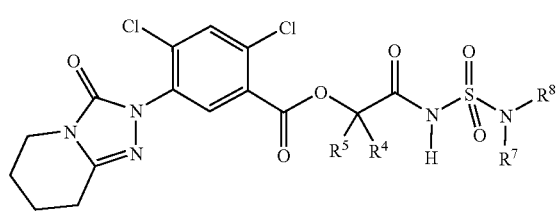
(I-Fd)

Among the compounds I-F preference is given to the 3-heterocyclyl-substituted benzoic acid derivatives of the formula I-Fb (≡I where $R^1$=II-E, $R^{24}$=difluoromethyl, $R^{25}$=methyl, $R^2$=Cl, $R^3$=Cl, $R^6$=H, X=O) in which $R^4$, $R^5$, $R^7$ and $R^8$ have the meanings mentioned above in particular the meanings mentioned as being preferred. Examples of such compounds are the compounds I-Fb.1 to I-Fb.600 in which the variables $R^4$, $R^5$, $R^7$ and $R^8$ together have the meanings given in one row of Table 1.

Among the compounds I-G preference is given to the 3-heterocyclyl-substituted benzoic acid derivatives of the formula I-Ga (≡I where $R^1$=II-G, $A^1$, $A^2$ are each oxygen, $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Ga.1 to I-Ga.600 in which the variables $R^4$, $R^5$, $R^7$ and $R^8$ together have the meanings given in one row of Table 1.

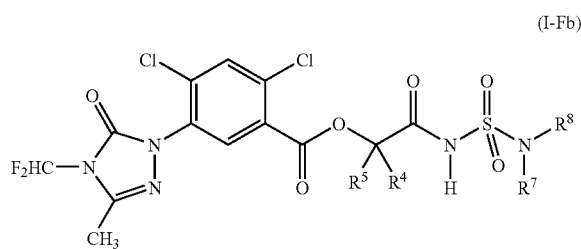
(I-Fb)

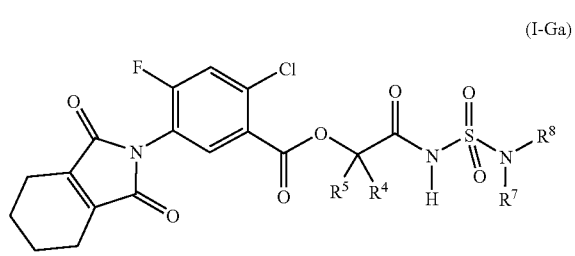
(I-Ga)

Among the compounds I-F preference is given to the 3-heterocyclyl-substituted benzoic acid derivatives of the formula I-Fc (≡I where $R^1$=II-F, $R^{24}$, $R^{25}$=(CH$_2$)$_4$, $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Fc.1 to I-Fc.600 in which the variables $R^4$, $R^5$, $R^7$ and $R^8$ together have the meanings given in one row of Table 1.

Among the compounds I-G preference is given to the 3-heterocyclyl-substituted benzoic acid derivatives of the formula I-Gb (≡I where $R^1$=II-G, $A^1$, $A^2$ are each oxygen, $R^2$=H, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Gb.1 to I-Gb.600 in which the variables $R^4$, $R^5$, $R^7$ and $R^8$ together have the meanings given in one row of Table 1.

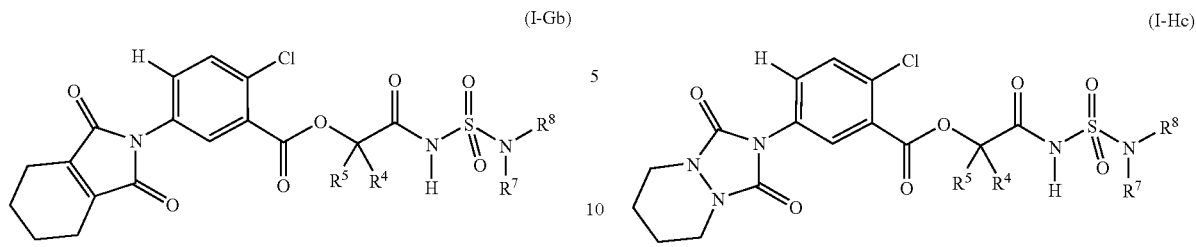

Among the compounds I-H preference is given to the 3-heterocyclyl-substituted benzoic acid derivatives of the formula I-Ha (≡I where $R^1$=II-H, $A^3$ and $A^4$ are each oxygen, $R^{26}$=difluoromethyl, $R^{27}$=methyl; $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Ha.1 to I-Ha.600 in which the variables $R^4$, $R^5$, $R^7$ and $R^8$ together have the meanings given in one row of Table 1.

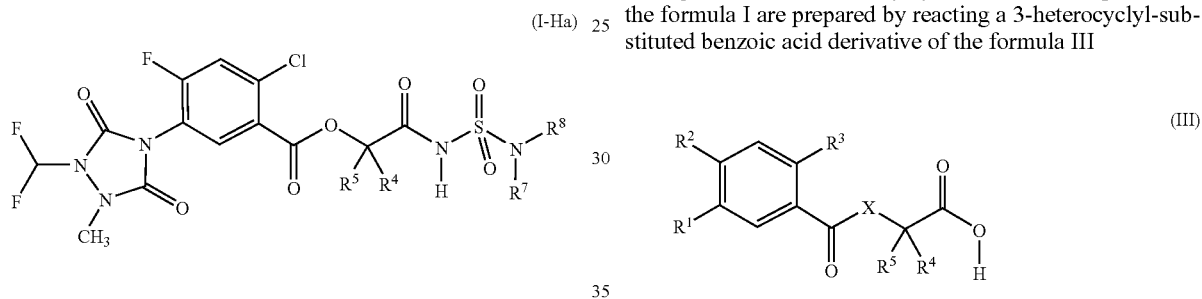

Among the compounds I-H preference is given to the 3-heterocyclyl-substituted benzoic acid derivatives of the formula I-Hb (≡I where $R^1$=II-H, $A^3$ and $A^4$ are each oxygen, $R^{26}$ and $R^{27}$ together are tetramethylene, $R^2$=F, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Hb.1 to I-Hb.600 in which the variables $R^4$, $R^5$, $R^7$ and $R^8$ together have the meanings given in one row of Table 1.

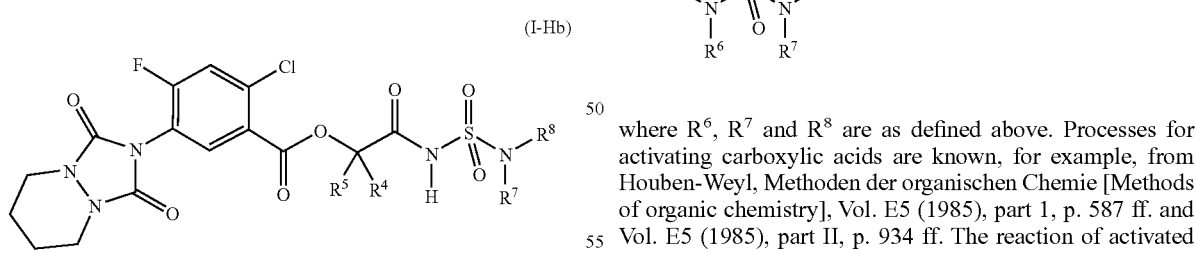

Among the compounds I-H preference is given to the 3-heterocyclyl-substituted benzoic acid derivatives of the formula I-Hc (≡I where $R^1$=II-H, $A^3$ and $A^4$ are each oxygen, $R^{26}$ and $R^{27}$ together are tetramethylene, $R^2$=H, $R^3$=Cl, $R^6$=H, X=O) in which $R^4$, $R^5$, $R^7$ and $R^8$ have the meanings mentioned above, in particular the meanings mentioned as being preferred. Examples of such compounds are the compounds I-Hc.1 to I-Hc.600 in which the variables $R^4$, $R^5$, $R^7$ and $R^8$ together have the meanings given in one row of Table 1.

The 3-heterocyclyl-substituted benzoic acid derivatives according to the invention can be prepared similarly to known processes. If no targeted synthesis of the isolation of pure isomers is carried out, the product may be obtained as a mixture of isomers. The mixtures can, if desired, be separated into the substantially pure isomers using methods customary for this purpose such as crystallization or chromatography, including chromatography on an optically active adsorbate. Pure optically active isomers can also be prepared, for example, from appropriate optically active starting materials.

In general, the 3-heterocyclyl-substituted compounds of the formula I are prepared by reacting a 3-heterocyclyl-substituted benzoic acid derivative of the formula III (III)

where $R^1$, $R^2$, $R^3$, $R^4$, $R^5$ and X are as defined above, if appropriate in the presence of a coupling agent, or by reacting the acid halide which corresponds to III, with a sulfamide of the formula IV

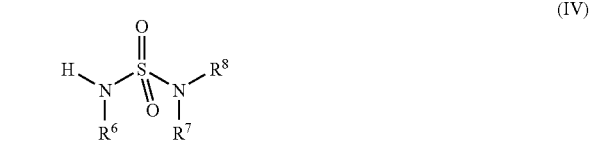

where $R^6$, $R^7$ and $R^8$ are as defined above. Processes for activating carboxylic acids are known, for example, from Houben-Weyl, Methoden der organischen Chemie [Methods of organic chemistry], Vol. E5 (1985), part 1, p. 587 ff. and Vol. E5 (1985), part II, p. 934 ff. The reaction of activated carboxylic acids III or carbonyl halides of III can be carried out analogously to the preparation of carboxylsulfamides described in WO 01/83459, for example in the manner described on p. 31 f.

Preferably, the carboxylic acid III is initially activated by reaction with a coupling agent. The activated carboxylic acid III is then, generally without prior isolation, reacted with the sulfamide IV. Suitable coupling agents are, for example, N,N'-carbonyldiimidazole or carbodiimides, such as dicyclohexylcarbodiimide. These are generally employed in at least equimolar amount and up to a fourfold excess, based on the carboxylic acid III. If appropriate, the resulting reaction mixture of carboxylic acid III and coupling agent is heated and then allowed to cool to room temperature. The reaction is usually carried out in a solvent. Suitable solvents are, for example, chlorinated hydrocarbons, such as methylene chloride or 1,2-dichloroethane, ethers, for example dialkyl ethers such as diethyl ether or methyl tert-butyl ether, or cyclic ethers, such as tetrahydrofuran or dioxane, carboxamides, such as dimethylformamide, N-methyllactams, such as N-methylpyrrolidone, nitriles, such as acetonitrile, aromatic hydrocarbons, such as toluene, aromatic amines, such as pyridine, or mixtures of these. This is followed by addition of the sulfamide IV. In general, the sulfamide IV is dissolved in the solvent which is also used for activating the carboxylic acid.

Alternatively, the carboxylic acid III can also initially be converted into the acid halide which corresponds to III, by using an inorganic acid halide, preferably by using an acid chloride such as thionyl chloride, phosphoryl chloride, phosphorus pentachloride, oxalyl chloride or phosphorus trichloride, and the acid halide formed is, if appropriate, isolated and then reacted with the sulfamide IV. If required, the reactivity of the thionyl chloride is increased by adding catalytic amounts of dimethylformamide. The halogenating agent is usually employed in at least equimolar amount, based on the carboxylic acid. The reaction partner thionyl chloride, phosphorus trichloride or phosphoryl chloride may simultaneously act as solvent. Suitable solvents are furthermore solvents which are inert under the reaction conditions, for example chlorinated hydrocarbons, such as methylene chloride and 1,2-dichloroethane, aromatic hydrocarbons, such as benzene or toluene, aliphatic and cycloaliphatic hydrocarbons, such as hexane, petroleum ether and cyclohexane, and mixtures thereof. The reaction temperature is generally between room temperature and the boiling point of the solvent. After the reaction has ended, excess halogenating agent is generally removed. The resulting acid chloride of III is then reacted with the sulfamide IV. In general, the sulfamide IV is dissolved in the solvent which was also used for preparing the carbonyl halide, unless the solvent is one of the acid halides mentioned above.

It is, of course, also possible to use other methods for activating the carboxylic acid. Such methods are described in the prior art.

The molar ratio of carboxylic acid III or the activated carboxylic acid which corresponds to III or of the acid chloride which corresponds to III to the sulfamide IV is generally at least 0.9:1, preferably at least 1:1. If appropriate, it may also be advantageous to employ a slight excess of sulfamide IV, for example in excesses up to 30%, based on the carboxylic acid III.

The reaction is usually carried out in the presence of a base which is preferably employed in an equimolar amount or an up to fourfold excess, based on the carboxylic acid III. Suitable bases are, for example, amines, such as 1,5-diazabicyclo[4.3.0]non-5-ene (DBN), 1,8-diazabicyclo[5.4.0]undec-7-ene (DBU), pyridine or triethylamine. If appropriate, it may be advantageous to carry out the reaction in the presence of a catalytic amount of 4-dimethylaminopyridine (DMAP). The added base is generally 5-10 mol %, based on the activated carboxylic acid III.

In general, the reaction temperature is in the range from 0° C. to the boiling point of the reaction mixture. Work-up can be carried out in a manner known per se.

The compounds of the formula IV can be obtained by processes known per se, for example by the processes described by G. Hamprecht in Angew. Chem. 93 (1981), 151-163 or by the processes described in WO 01/83459, DE 102 21 910.9 or in Houben-Weyl, Vol. E11 (1985), p. 1019.

3-Heterocyclyl-substituted benzoic acid derivatives of the formula III are known in the prior art or can be prepared similarly to known processes, frequently from the esters that correspond to III.

In this case, the esters are converted into the corresponding carboxylic acids III according to known processes by hydrolysis in acidic media using strong mineral acids, such as concentrated hydrochloric acid or sulfuric acid, or organic acids, such as glacial acetic acids, or mixtures thereof. Alternatively, esters can also be hydrolyzed in an alkaline media using bases such as alkali metal hydroxides, for example sodium hydroxide or potassium hydroxide in the presence of water.

Solvents suitable both for the acid- and the base-catalyzed hydrolysis of esters include, for example, chlorinated aliphatic or alicyclic hydrocarbons, such as methylene chloride or 1,2-dichloroethane, or alcohols. In the case of the acid-catalyzed hydrolysis, the reaction partner usually simultaneously acts as solvent and is therefore employed in excess, based on the ester. The reaction temperature is usually between room temperature and the boiling point of the solvent.

Esters of the carboxylic acid III where $R^1$ is a heterocyclic radical of the formula II-A are known, for example, from U.S. Pat. No. 6,207,830 and DE 197 41 411. Esters of carboxylic acids of the formula III where $R^1$ is a heterocyclic radical of the formula II-C are known from WO 97/11059. Esters of carboxylic acids of the formula III where $R^1$ is a radical II-E are known, for example, from WO 92/06962 and JP 09059113. Esters of carboxylic acids of the formula II-F are known, for example, from JP 61069776. Compounds III which are not explicitly described in these publications can be prepared similarly to these processes.

If the esters of carboxylic acids of the formula III are not known, they can be prepared, for example, by reacting a 3-heterocyclyl-substituted benzoic acid of the formula V

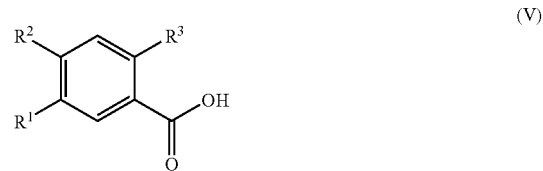

(V)

where $R^1$, $R^2$ and $R^3$ are defined above with an α-aminocarboxylic acid ester or an α-hydroxycarboxylic acid ester of the formula VI $$HXC(R^4)(R^5)COOR'$$ (VI)

where X, $R^4$ and $R^5$ are as defined above and R' is lower alkyl, in the presence of a dehydrating agent, such as N,N'-carbonyldiimidazole or dicyclohexylcarbodiimide. Alternatively, it is also possible to initially convert the benzoic acid of the formula V into its acid halide, followed by reaction with the compound of the formula VI.

The reaction conditions correspond substantially to the conditions mentioned above for the reaction of III with IV. The reaction is usually carried out in a solvent. Suitable solvents are chlorinated hydrocarbons, such as methylene chloride and 1,2-dichloroethane, ethers, such as diethyl ether, methyl tert-butyl ether, tetrahydrofuran and dioxane, or mixtures of these. The reaction with a compound of the formula VI is usually carried out at a temperature between room temperature and the boiling point of the solvent. The resulting ester of III is then hydrolyzed, giving the desired 3-heterocyclyl-substituted carboxylic acid III. With respect to the practice of the hydrolysis, reference is made to what was said above.

The carboxylic acid V can be prepared, for example, according to WO 01/083459 or the prior art cited therein, or similarly to the processes described therein. If appropriate, the ester described in the prior art has to be converted by known methods into the carboxylic acid V. With respect to the acid- or base-catalyzed hydrolysis of esters, reference is made to what was said above. The following publications are expressly referred to:

WO 88/10254, WO 89/02891, WO 89/03825, WO 91/00278 (compounds of the formula V or their esters where $R^1$ is a heterocyclic radical of the formula II-A), EP 0 584 655, WO 00/050409 (the esters of the compounds of the formula V where $R^1$ is a heterocyclic radical of the formula II-B), WO 96/39392, WO 97/07104 (compounds of the formula V and/or the ester corresponding to V, where $R^1$ is a heterocyclic radical of the formula II-D), WO 92/06962 (compounds of the formula V where $R^1$ is a heterocyclic radical of the formula II-E).

The compounds I and their agriculturally useful salts are suitable—both as isomer mixtures and in the form of the pure isomers—as herbicides. Herbicides containing I permit very good control of plant growth on uncultivated areas. In crops such as wheat, rice, corn, soybean and cotton, they are effective against broad-leaved weeds and harmful grasses without significantly damaging the crops. This effect occurs in particular at low application rates.

Depending on the particular application method, the compounds I or the herbicidal compositions comprising them may be used in a further number of crops for eliminating unwanted plants. Suitable are, for example, the following crops:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera* and *Zea mays.*

The compounds I may also be used in crops which are tolerant to the action of herbicides as a result of breeding, including the use of genetic engineering methods.

Furthermore, the compounds I and their agriculturally useful salts are suitable for the desiccation and/or defoliation of plants.

As desiccants, they are particularly suitable for drying out the above-ground parts of crops, such as potatoes, rape, sunflower and soybeans. This permits completely mechanical harvesting of these important crops.

Also of commercial interest is the concentrated dropping of fruits or the reduction of their adhesion to the plant, for example, in the case of citrus fruits, olives or other species and varieties of pomes, drupes and hard-shelled fruit, since because of this, the harvesting of these fruits is made easier, and the controlled defoliation of useful plants, in particular cotton.

The dropping brought about by the use of novel active compounds of the formula I depends on the formation of abscission tissue between fruit or leaf part, and shoot part of the plants.

The defoliation of cotton is of very particular commercial interest, since it makes the harvest easier. At the same time, the shortening of the period in which the individual plants ripen leads to an improved quality of the harvested fiber material.

The compounds I or the herbicidal compositions comprising them can be used, for example, in the form of directly sprayable aqueous solutions, powders, suspensions, including highly concentrated aqueous, oily or other suspensions or dispersions, emulsions, oil dispersions, pastes, dusting agents, broadcasting agents or granules, by spraying, nebulizing, dusting, broadcasting or pouring, or for seed dressing or mixing with the seed. The application forms depend on the intended uses; they should in any case ensure very fine distribution of the active ingredients according to the invention.

The herbicides contain a herbicidally effective amount of at least one active compounds of the formula I and auxiliaries which are usually used in formulating crop protection agents.

Suitable inert auxiliaries are essentially:

mineral oil fractions having a medium to high boiling point, such as kerosine and diesel oil, and coal tar oils and oils of vegetable or animal origin, aliphatic, cyclic and aromatic hydrocarbons, for example paraffins, tetrahydronaphthalene, alkylated naphthalenes and derivatives thereof, alkylated benzenes and derivatives thereof, alcohols, such as methanol, ethanol, propanol, butanol and cyclohexanol, ketones, such as cyclohexanone, and strongly polar solvents, for example amines, such as N-methylpyrrolidone, and water.

Aqueous application forms can be prepared from emulsion concentrates, from suspensions, pastes, wettable powders or water-dispersible granules by adding water. For the preparation of emulsions, pastes or oil dispersions, the 3-heterocyclyl-substituted benzoic acid derivatives I, as such or dissolved in an oil or solvent, can be homogenized in water by means of wetting agents, adherents, dispersants or emulsifiers. However, it is also possible to prepare concentrates which consist of active ingredients, wetting agents, adherents, dispersants or emulsifiers and possibly solvent or oil, which are suitable for dilution with water.

Suitable surfactants are the alkali metal, alkaline earth metal and ammonium salts of aromatic sulfonic acids, e.g. lignin-, phenol-, naphthalene- and dibutylnaphthalenesulfonic acid, and fatty acids, alkylsulfonates and alkylarylsulfonates, alkyl sulfates, lauryl ether sulfates and fatty alcohol sulfates, and salts of sulfated hexa-, hepta- and octadecanols and of fatty alcohol glycol ether, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders and other solid carriers.

The concentrations of the active ingredients I in the ready-to-use formulations may be varied within wide ranges. In general, the formulations contain from about 0.001 to 98, preferably from 0.01 to 95, % by weight of at least one active ingredient I. The active ingredients are used in a purity of from 90 to 100%, preferably from 95 to 100% (according to the NMR spectrum).

The compounds I according to the invention can be formulated, for example, as follows:

I. 20 parts by weight of a compound I are dissolved in a mixture which consists of 80 parts by weight of alkylated benzene, 10 parts by weight of the adduct of from 8 to 10 mol of ethylene oxide with 1-mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

II. 20 parts by weight of a compound I are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of a compound I are dissolved in a mixture which consists of 25 parts by weight of cyclohexanone, 65 parts by weight of a mineral oil fraction boiling within the range from 210 to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of a compound I are thoroughly mixed with 3 parts by weight of the sodium salt of diisobutylnaphthalene-α-sulfonic acid, 17 parts by weight of the sodium salt of a lignosulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

V. 3 parts by weight of a compound I are mixed with 97 parts by weight of finely divided kaolin. A dusting agent which contains 3% by weight of the active ingredient is obtained in this manner.

VI. 20 parts by weight of a compound I are thoroughly mixed with 2 parts by weight of the calcium salt of dodecylbenzenesulfonic acid, 8 parts by weight of a fatty alcohol polyglycol ether, 2 parts by weight of sodium salt of a phenol/urea/formaldehyde condensate and 68 parts by weight of a paraffinic mineral oil. A stable oily dispersion is obtained.

VII. 1 part by weight of a compound I is dissolved in a mixture which consists of 70 parts by weight of cyclohexanone, 20 parts by weight of ethoxylated isooctylphenol and 10 parts by weight of ethoxylated castor oil. A stable emulsion concentrate is obtained.

VIII. 1 part by weight of a compound I is dissolved in a mixture which consists of 80 parts by weight of cyclohexanone and 20 parts by weight of Wettol® EM31 (=nonionic emulsifier based on ethoxylated castor oil; BASF AG). A stable emulsion concentrate is obtained.

The active compounds I or the herbicidal compositions can be applied by the preemergence or postemergence method. The herbicidal compositions or active compounds can also be applied by sowing crop seed which has been pretreated with the herbicidal compositions or active compounds. If the active ingredients are less well tolerated by certain crops, it is possible to use application methods in which the herbicides are sprayed with the aid of the sprayers in such a way that the leaves of the sensitive crops are as far as possible not affected, while the active compounds reach the leaves of undesirable plants growing underneath or the uncovered soil surface (post-directed, lay-by).

The application rates of active compound I are from 0.001 to 3.0, preferably from 0.01 to 1.0, kg/ha of active ingredient (a.i.), depending on the aim of control, the season, the target plants and the state of growth.

In order to broaden the action spectrum and to achieve synergistic effects, the 3-heterocyclyl-substituted benzoic acid derivatives I may be mixed with many members of other groups of herbicidal or growth-regulating active ingredients and applied together with them.

Examples of suitable components of the mixture are 1,2, 4-thiadiazoles, 1,3,4-thiadiazoles, amides, aminophosphoric acid and derivatives thereof, aminotriazoles, anilides, aryloxy-/hetaryloxyalkanoic acids and derivatives thereof, benzoic acid and derivatives thereof, benzothiadiazinones, 2-(hetaroyl/aroyl)-1,3-cyclohexanediones, hetarylarylketones, benzylisoxazolidinones, meta-$CF_3$-phenyl derivatives, carbamates, quinolinecarboxylic acid and derivatives thereof, chloroacetanilides, cyclohexane-1,3-dione derivatives, diazines, dichloropropionic acid and derivatives thereof, dihydrobenzofurans, dihydrofuran-3-ones, dinitroanilines, dinitrophenols, diphenyl ethers, dipyridyls, halocarboxylic acids and derivatives thereof, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and derivatives thereof, 2-phenylpropionic acid and derivatives thereof, pyrazoles, phenylpyrazoles, pyridazines, pyridinecarboxylic acid and derivatives thereof, pyrimidyl ethers, sulfonamides, sulfonylureas, triazines, triazinones, triazolinones, triazolcarboxamides and uracils.

It may also be useful to apply the compounds I together, alone or in combination with other herbicides, also as a mixture with further crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates can also be added.

The examples below are intended to illustrate the invention without limiting it.

PREPARATION EXAMPLES

Example 1

(S)-2-[2-Chloro-5-(3-methyl-2,6-dioxo-4-trifluoro methyl-3,6-dihydro-2H-pyrimidin-1-yl)-4-fluorobenzoyloxy]propionic acid N,N-dimethylsulfamide (S-enantiomer of compound I-Aa. 242)

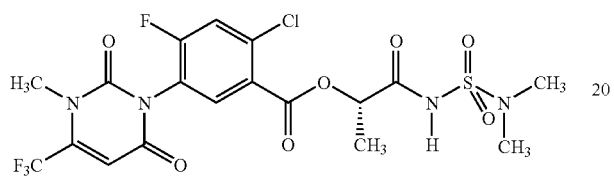

I-Aa.242

1.1: 2-Chloro-4-fluoro-5-(3-methyl-2,6-dioxo-4-trifluoromethyl-3,6-dihydro-2H-pyrimidin-1-yl)benzoic acid 13.9 g (34 mmol) of isopropyl 2-chloro-4-fluoro-5-(3-methyl-2,6-dioxo-4-trifluoromethyl-3,6-dihydro-2H-pyrimidin-1-yl)benzoate (CAS No. 105756-82-9, U.S. Pat. No. 5,176,735, U.S. Pat. No. 4,943,309, WO 88/10254) were dissolved in 100 ml of glacial acetic acid and 100 ml of conc. HCl, and the mixture was heated at 70° C. for 15 hours. The acetic acid was removed under reduced pressure, the residue was taken up in water and the resulting precipitate was filtered off with suction. Drying gave 11.3 g of the uracilcarboxylic acid which was used for the next step without further purification.

$^1$H-NMR (DMSO-$d_6$) δ (ppm)=8.1 (d, 1H), 7.8 (d, 1H), 6.6 (s, 1H), 3.4 (s, 3H).

1.2: Methyl (S)-2-[2-chloro-5-(3-methyl-2,6-dioxo-4-trifluoro methyl-3,6-dihydro-2H-pyrimidin-1-yl)-4-fluorobenzoyloxy]propionate 5.0 g (13.64 mmol) of uracilcarboxylic acid from 1.1 in 50 ml of thionyl chloride were heated at reflux for 3 h, and unreacted thionyl chloride was then removed under reduced pressure. The resulting acid chloride was then dissolved in 50 ml of methylene chloride, and the resulting solution was, at 0-5° C., added dropwise with stirring to a solution of 1.6 g (15.01 mmol) of methyl (S)-lactate, 0.2 g (1.36 mmol) of 4-dimethylaminopyridine (DMAP) and 1.7 g (16.37 mmol) of triethylamine in 80 ml of CH$_2$Cl$_2$. The mixture was allowed to warm to room temperature and stirred at room temperature for another 16 hours. The reaction mixture was then concentrated and chromatographed on silica gel using cyclohexane/ethyl acetate 70/30. The solvent was evaporated under reduced pressure, giving 5.85 g of the ester.

$^1$H-NMR (DMSO-$d_6$) δ (ppm)=8.0 (d, 1H), 7.4 (d, 1H), 6.4 (s, 1H), 5.4 (q, 1H), 4.8 (s, 3H), 3.6 (s, 3H), 1.5 (d, 3H).

1.3: (S)-2-Chloro-5-(3-methyl-2,6-dioxo-4-trifluoromethyl-3,6-dihydro-2H-pyrimidin-1-yl)-4-fluorobenzoyloxy]propionic acid 25 ml of glacial acetic acid and 25 ml of conc. HCl were added to 3.6 g (8 mmol) of the ester from 1.2, the mixture was heated at 60° C. for 4 hours and then stirred at room temperature for 8 hours. The acetic acid was removed under reduced pressure and the reaction mixture was diluted with water and extracted three times with in each case about 150 ml of ethyl acetate. The combined organic phases were then dried over Na$_2$SO$_4$ and concentrated under reduced pressure, giving 3.3 g of acid.

$^1$H-NMR (DMSO-$d_6$) δ (ppm)=8.0 (d, 1H), 7.4 (d, 1H), 6.4 (s, 1H), 5.4 (q, 1H), 3.5 (s, 3H), 1.6 (d, 3H).

1.4: (S)-2-[2-Chloro-5-(3-methyl-2,6-dioxo-4-trifluoromethyl-3,6-dihydro-2H-pyrimidin-1-yl)-4-fluorobenzoyloxy]propionic acid N,N-dimethylsulfamide 0.45 g (1.03 mmol) of the acid from 1.3 in 10 ml of thionyl chloride was heated at reflux for 3 hours and excess thionyl chloride was then removed under reduced pressure and the resulting acid chloride was dissolved in about 5 ml of CH$_2$Cl$_2$. This solution was, at about 5° C., added dropwise to a solution of 0.13 g (1.03 mmol) of N,N-dimethylsulfamide, 0.23 g (2.23 mmol) of triethylamine and a catalytic amount of DMAP in 20 ml of CH$_2$Cl$_2$. The reaction mixture was stirred at room temperature for 14 hours and then concentrated under reduced pressure. The residue was taken up in ethyl acetate and washed with about 200 ml of 10% strength hydrochloric acid. Chromatography on silica gel using cyclohexane/ethyl acetate 70/30 gave 0.16 g of the title compound of m.p. 207-208° C.

$^1$H-NMR: see Table 2

Example 2

2-[2-Chloro-5-(3-methyl-2,6-dioxo-4-trifluoro-methyl-3,6-dihydro-2H-pyrimidin-1-yl)benzoyloxy]-2-methyl-propionic acid N-methyl-N-allylsulfamide (compound I-Ab.465)

0.33 g (2.2 mmol) of N-methyl-N-allylsulfamide, 0.27 g of 4-dimethylaminopyridine and 0.64 ml of triethylamine were dissolved in 10 ml of dichloromethane. A solution of 0.98 g (2.2 mmol) of 2-[2-chloro-5-(3-methyl-2,6-dioxo-4-trifluoro-methyl-3,6-dihydro-2H-pyrimidin-1-yl)benzoyloxy]-2-methyl-propionyl chloride (CAS No. 160152-72-7) in dichloromethane was then added dropwise. The solution was stirred for 3 days and then concentrated, and the residue was taken up in ethyl acetate. The organic phase was washed with 10% strength hydrochloric acid and water and dried over sodium sulfate, the drying agent was filtered off and the filtrate was concentrated. Column chromatography on silica gel (mobile phase: cyclohexane/ethyl acetate 2:1) gave 0.21 g of the title compound of melting point 161-164° C.

Example 3

(S)-2-[2-Chloro-5-(3-methyl-2,6-dioxo-4-trifluoromethyl-3,6-dihydro-2H-pyrimidin-1-yl)benzoyloxy] propionic acid N-methyl-N-allylsulfamide (S enantiomer of compound I-Ab.265)

3.1: Methyl (S)-2-[2-chloro-5-(3-methyl-2,6-dioxo-4-trifluoro-methyl-3,6-dihydro-2H-pyrimidin-1-yl) benzoyloxy]propionate 7.0 g (20 mmol) of 2-chloro-5-(3-methyl-2,6-dioxo-4-trifluoromethyl-3,6-dihydro-2H-pyrimidin-1-yl)benzoic acid (CAS No. 120890-58-6) were dissolved in 50 ml of thionyl chloride. The reaction mixture was then heated under reflux for 3 hours, and the resulting solution of the acid chloride was concentrated. 2.3 g (22 mmol) of methyl (S)-lactate, 2.46 g (20 mmol) of 4-dimethylaminopyridine and 2.44 g (20 mmol) of triethylamine were then dissolved in 50 ml of dichloromethane, and a solution of the acid chloride obtained above in dichloromethane was then added dropwise at 0° C. The reaction mixture was stirred at room temperature for 16 hours, and the solution was then concentrated. Column chromatography on silica gel (mobile phase: cyclohexane/ethyl acetate 2:1) gave 7.0 g of methyl (S)-2-[2-chloro-5-(3-methyl-2,6-dioxo-4-trifluoromethyl-3,6-di-hydro-2H-pyrimidin-1-yl)benzoyloxy]propionate of melting point 59-60° C.

3.2: (S)-2-[2-Chloro-5-(3-methyl-2,6-dioxo-4-trifluoromethyl-3,6-dihydro-2H-pyrimidin-1-yl)benzoyloxy]propionic acid 7.0 g (16 mmol) of methyl (S)-2-[2-chloro-5-(3-methyl-2,6-di-oxo-4-trifluoromethyl-3,6-dihydro-2H-pyrimidin-1-yl)benzoyl-oxy]propionate from example 3.1 were dissolved in 50 ml of acetic acid, 50 ml of conc. hydrochloric acid were added and the solution was heated under reflux for 4 hours. Most of the acetic acid was distilled off, and the solution that remained was poured onto ice-water. The aqueous phase was extracted three times with ethyl acetate, the organic phase was dried over sodium sulfate, the drying agent was filtered off and the filtrate was concentrated to dryness, which gave 5.7 g of (S)-2-[2-chloro-5-(3-methyl-2,6-dioxo-4-trifluoromethyl-3,6-dihydro-2H-pyrimidin-1-yl)benzoyloxy]propionic acid.

3.3: (S)-2-[2-Chloro-5-(3-methyl-2,6-dioxo-4-trifluoromethyl-3,6-dihydro-2H-pyrimidin-1-yl)benzoyloxy]propionyl chloride 5.7 g (14 mmol) of (S)-2-[2-chloro-5-(3-methyl-2,6-dioxo-4-trifluoromethyl-3,6-dihydro-2H-pyrimidin-1-yl)benzoyloxy]-propionic acid from example 3.2 were dissolved in 50 ml of thionyl chloride, and the reaction mixture was heated under reflux for 3.5 hours. The solution was allowed to cool and concentrated, which gave 5.9 g of (S)-2-[2-chloro-5-(3-methyl-2,6-dioxo-4-trifluoromethyl-3,6-dihydro-2H-pyrimidin-1-yl)-benzoyloxy]propionyl chloride.

3.4: (S)-2-[2-Chloro-5-(3-methyl-2,6-dioxo-4-trifluoromethyl-3,6-dihydro-2H-pyrimidin-1-yl)benzoyloxy]propionic acid N-methyl-N-allylsulfamide 0.33 g (2.2 mmol) of N-methyl-N-allylsulfamide, 0.27 g of 4-dimethylaminopyridine and 0.67 ml of triethylamine were dissolved in 10 ml of dichloromethane, and a solution of 0.98 g (2.2 mmol) of (S)-2-[2-chloro-5-(3-methyl-2,6-dioxo-4-trifluoro-methyl-3,6-dihydro-2H-pyrimidin-1-yl)benzoyloxy] propionyl chloride from example 3.3 in 10 ml of dichloromethane was added dropwise. The solution was stirred for 16 hours and then concentrated, and the resulting residue was dissolved in ethyl acetate. The organic phase was washed with 10% strength hydrochloric acid and water and dried over sodium sulfate, the drying agent was filtered off and the filtrate was concentrated. Column chromatography on silica gel gave 0.26 g of the title compound.

Example 4

2-[2-Chloro-5-(3-methyl-2,6-dioxo-4-trifluoromethyl-3,6-dihydro-2H-pyrimidin-1-yl)-4-fluorobenzoyloxy]-2-methyl-propionic acid N,N-dimethyl-N-allylsulfamide (compound I-Aa.442)

4.1: Methyl 2-[2-chloro-5-(3-methyl-2,6-dioxo-4-trifluoro-methyl-3,6-dihydro-2H-pyrimidin-1-yl)-4-fluorobenzoyloxy]-2-methylpropionate 0.61 g (5.2 mmol) of methyl 2-hydroxy-2-methylpropionate, 70 mg (0.5 mmol) of 4-N-pyrrolidinopyridine and 0.87 ml (6.2 mmol) of triethylamine were dissolved in 50 ml of tetrahydrofuran, and a solution of 2 g (5.2 mmol) of the acid chloride from example 1.2 in 50 ml of tetrahydrofuran were then added dropwise. The solution was stirred for 16 hours and then concentrated, and the residue was then dissolved in ethyl acetate. The organic phase was washed with 10% strength citric acid and water and dried over sodium sulfate, the drying agent was filtered off and the filtrate was concentrated. Column chromatography on silica gel (mobile phase: cyclohexane/ethyl acetate 2:1) gave 1.0 g of methyl 2-[2-chloro-5-(3-methyl-2,6-dioxo-4-trifluoromethyl-3,6-dihydro-2H-pyrimidin-1-yl)-4-fluorobenzoyloxy]-2-methyl-propionate.

4.2: 2-[2-Chloro-5-(3-methyl-2,6-dioxo-4-trifluoromethyl-3,6-dihydro-2H-pyrimidin-1-yl)-4-fluorobenzoyloxy]-2-methyl-propionic acid 1.0 g (2.1 mmol) of methyl 2-[2-chloro-5-(3-methyl-2,6-dioxo-4-trifluoromethyl-3,6-dihydro-2H-pyrimidin-1-yl)-4-fluoro-benzoyloxy]-2-methylpropionate from example 4.1 was dissolved in 50 ml of acetic acid, 50 ml of conc. hydrochloric acid were added and the reaction mixture was heated under reflux for 5 hours. Most of the acetic acid was distilled off, and the solution that remained was poured into ice-water. The precipitate was filtered off and dried, which gave 0.65 g of 2-[2-chloro-5-(3-methyl-2,6-dioxo-4-trifluoromethyl-3, 6-dihydro-2H-pyrimidin-1-yl)-4-fluorobenzoyloxy]-2-methylpropionic acid.

4.3: 2-[2-Chloro-5-(3-methyl-2,6-dioxo-4-trifluoromethyl-3,6-di-hydro-2H-pyrimidin-1-yl)-4-fluorobenzoyloxy]-2-methylpropionic acid N,N-dimethylsulfamide 0.65 g (1.4 mmol) of 2-[(2-chloro-5-(3-methyl-2,6-dioxo-4-trifluoromethyl-3,6-dihydro-2H-pyrimdin-1-yl)-4-fluorobenzoyloxy]-2-methylpropionic acid from example 4.2 was dissolved in 30 ml of thionyl chloride, the reaction mixture was heated under reflux for 3 hours and the resulting solution of the acid chloride was then concentrated. 0.18 g (1.4 mmol) of N,N-dimethylsulfamide, 0.07 g (1.4 mmol) of 4-dimethylaminopyridine and 0.35 ml (3.5 mmol) of triethylamine were dissolved in 10 ml of dichloromethane, and a solution of the acid chloride which had been prepared beforehand in 10 ml of dichloromethane was then added dropwise. The solution was stirred for 16 hours and then concentrated, and the residue was then dissolved in ethyl acetate. The organic phase was washed with 10% strength hydrochloric acid and water, the organic phase was dried over sodium sulfate, the drying agent was filtered off and the filtrate was concentrated. Column chromatography on silica gel (mobile phase: cyclohexane/ethyl acetate 2:1) gave 0.30 g of the title compound of melting point 211-213° C.

In addition to the benzoic acid derivatives of the formula I described above, Table 2 below lists further compounds of the formula I which were prepared analogously.

TABLE 2

| No. | $^1$H-NMR δ [ppm], | m.p. [° C.] |
|---|---|---|
| S-enantiomer of the compound I-Aa.242 | (CDCl$_3$): 8.7(br., 1H), 8.0(m, 1H), 7.5(d, 1H), 6.4(s, 1H), 5.4(m, 1H), 3.5(s, 3H), 2.9(s, 6H), 1.6(d, 3H). | 207–208 |
| S-enantiomer of the compound I-Aa.243 | (CDCl$_3$): 8.7(br., 1H), 8.0(m, 1H), 7.5(d, 1H), 6.4(s, 1H), 5.4(m, 1H), 3.5(s, 3H), 3.4(q, 2H), 2.9(s, 3H), 1.6(d, 3H), 1.3(t, 3H), | 170–171 |
| S-enantiomer of the compound I-Aa.246 | (CDCl$_3$): 8.7(br., 1H), 8.0(m, 1H), 7.5(d, 1H), 6.4(s, 1H), 5.4(m, 1H), 4.2(m, 1H), 3.5(s, 3H), 2.9(s, 3H), 1.6(d, 3H), 1.3(d, 6H). | 164–165 |
| S-enantiomer of the compound I-Aa.251 | (CDCl$_3$): 8.7(br., 1H), 8.0(m, 1H), 7.5(d, 1H), 6.4(s, 1H), 5.4(m, 1H), 3.6–3.4(m, 7H), 3.3(s, 3H), 2.9(s, 3H), 1.6(d, 3H). | 132–134 |
| S-enantiomer of the compound I-Aa.265 | (CDCl$_3$): 8.7(br., 1H), 8.0(m, 1H), 7.5(d, 1H), 6.4(s, 1H), 5.9–5.8(m, 1H), 5.5–5.1(m, 3H), 3.9(d, 1H), 3.5(s, 3H), 2.9(s, 3H), 1.6(d, 3H). | 129–130 |
| S-enantiomer of the compound I-Aa.269 | (CDCl$_3$): 8.7(br., 1H), 8.0(m, 1H), 7.5(d, 1H), 6.4(s, 1H), 5.4(m, 1H), 4.2(m, 2H), 3.5(s, 3H), 2.9(s, 3H), 2.3(m, 1H), 1.6(d, 3H). | |
| I-Ab.465 | (DMSO-d$_6$): 11.7(br. s, 1H), 7.9(m, 1H), 7.7(m, 1H), 7.6(m, 1H), 6.6(s, 1H), 5.8(m, 1H), 5.3–5.2(m, 2H), 3.8(d, 2H), 3.4(s, 3H), 2.8(s, 3H), 1.6(s, 6H). | 161–164 |
| I-Ab.469 | (DMSO-d$_6$): 11.7(br. s, 1H), 7.9(m, 1H), 7.7(m, 1H), 7.6(m, 1H), 6.6(s, 1H), 4.1(d, 2H), 3.4(s, 3H), 3.3(t, 3H), 2.8(s, 3H), 1.6(s, 6H). | |
| I-Ab.442 | (DMSO-d$_6$): 11.7(br. s, 1H), 7.9(m, 1H), 7.7(m, 1H), 7.6(m, 1H), 6.6(s, 1H), 4.0(m, 1H), 3.4(s, 3H), 2.8(s, 6H), 1.6(s, 6H). | |
| S-enantiomer of compound I-Ab.248 | | oil |
| S-enantiomer of compound I-Ab.242 | | oil |
| S-enantiomer of compound I-Ab.243 | | oil |
| S-enantiomer of compound I-Ab.265 | | oil |
| I-Ab.443 | | 193–194 |
| I-Ab.446 | | 177–179 |
| I-Ab.448 | | 140–142 |
| I-Aa.442 | (DMSO-d$_6$): 11.63(s, 1H), 8.13(d, 1H), 7.91(d, 1H), 6.63(s, 1H), 3.42(s, 3H), 2.84(s, 6H), 1.61(s, 6H) | 211–213 |

Use Examples

The herbicidal activity of the 3-heterocyclyl-substituted benzoic acid derivatives I was demonstrated by the following greenhouse experiments:

The cultivation containers used were plastic flowerpots containing loamy sand with approximately 3.0% of humus as the substrate. The seeds of the test plants were sown separately for each species.

For the preemergence treatment, directly after sowing the active compounds, which had been suspended or emulsified in water, were applied by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the postemergence treatment, the test plants were first grown to a height of 3-15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to the treatment. The application rate for the postemergence treatment was 7.8 or 3.9 g of a.i. (active ingredient)/ha.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0.0 to 100. 100 means no emergence of the plants, or complete destruction of at least the above-ground parts, and 0 means no damage, or normal course of growth.

The plants used in the greenhouse experiments were of the following species:

| Scientific name | Common name |
|---|---|
| *Amaranthus retroflexus* | redroot pigweed |
| *Chenopodium album* | lambsquarters (goosefoot) |

Applied by the postemergence method, the S enantiomer of the compound I-Aa.246 showed excellent herbicidal activity against the abovementioned plants.

Use Examples

Desiccant/Defoliant Action

The test plants used were young cotton plants with 4 leaves (without cotyledons) which had been grown under greenhouse conditions (rel. atmospheric humidity 50-70%; day/night temperature 27/20° C.).

The young cotton plants were subjected to foliar treatment to runoff point with aqueous preparations of the active compounds (with addition of 0.15% by weight, based on the spray mixture, of the fatty alcohol alkoxylate Plurafac® LF 700[1])). The amount of water applied was 1000 l/ha (converted). After 13 days, the number of leaves shed and the degree of defoliation in % were determined.

1) a low-foam, nonionic surfactant from BASF AG

The untreated control plants did not shed any leaves.

We claim:

1. A 3-heterocyclyl-substituted benzoic acid compound of the formula I

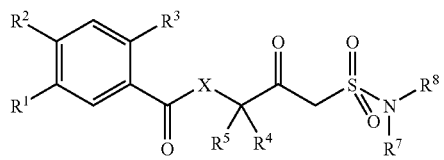

wherein:

X is oxygen or $NR^9$, $R^1$ is a heterocyclic radical of the formulae II-A to II-D,

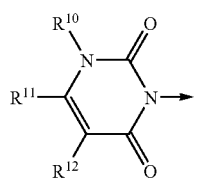

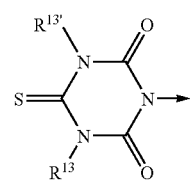

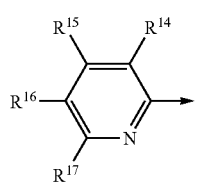

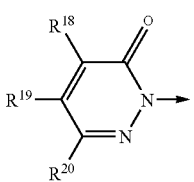

$R^2$ is hydrogen or halogen, $R^3$ is halogen or cyano, $R^4$, $R^5$ independently of one another are hydrogen, $C_1$-$C_4$-alkyl or $C_1$-$C_4$-alkoxy, or $R^4$ and $R^5$ together are a group $=CH_2$, $R^6$ is hydrogen, $C_1$-$C_4$-alkyl or $C_1$-$C_4$-alkoxy, $R^7$, $R^8$ independently of one another are hydrogen, $C_1$-$C_6$-alkyl, $C_3$-$C_6$-alkenyl, $C_3$-$C_6$-alkynyl, $C_1$-$C_4$-haloalkyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl, cyano-$C_1$-$C_4$-alkyl, $C_1$-$C_4$-alkoxycarbonyl-$C_1$-$C_4$-alkyl, amino-$C_1$-$C_4$-alkyl, $C_1$-$C_4$-alkylamino-$C_1$-$C_4$-alkyl, di($C_1$-$C_4$-alkyl)amino-$C_1$-$C_4$-alkyl, aminocarbonyl-$C_1$-$C_4$-alkyl, ($C_1$-$C_4$-alkylamino)carbonyl-$C_1$-$C_4$-alkyl, di($C_1$-$C_4$-alkyl)aminocarbonyl-$C_1$-$C_4$-alkyl, phenyl or $C_1$-$C_4$-alkylphenyl or $R^9$ is hydrogen, hydroxyl, $C_1$-$C_4$-alkyl, $C_1$-$C_4$-alkoxy, phenyl, phenyl-$C_1$-$C_4$-alkyl, $C_3$-$C_6$-alkenyl or $C_3$-$C_6$-alkynyl, $R^{10}$ is hydrogen, $C_1$-$C_4$-alkyl or amino, $R^{11}$ is $C_1$-$C_4$-alkyl or $C_1$-$C_4$-haloalkyl, $R^{12}$ is hydrogen or $C_1$-$C_4$-alkyl, $R^{13}$, $R^{13'}$ independently of one another are hydrogen or $C_1$-$C_4$-alkyl, $R^{14}$ is halogen, $R^{15}$ is hydrogen or $C_1$-$C_4$-alkyl, $R^{16}$ is $C_1$-$C_4$-haloalkyl, $C_1$-$C_4$-alkylthio, $C_1$-$C_4$-alkylsulfonyl or $C_1$-$C_4$-alkylsulfonyloxy, $R^{17}$ is hydrogen or $C_1$-$C_4$-alkyl, $R^{18}$ is hydrogen, C1-C4-alkyl or amino, $R^{19}$ is $C_1$-$C_4$-haloalkyl, $C_1$-$C_4$-alkylthio or $C_1$-$C_4$-alkylsulfonyl, $R^{20}$ is hydrogen or $C_1$-$C_4$-alkyl, $R^{21}$ is hydrogen, halogen or $C_1$-$C_4$-alkyl, or an agriculturally useful salt thereof.

2. A benzoic acid compound as claimed in claim 1 where $R^2$ is fluorine, chlorine or hydrogen.

3. A benzoic acid compound as claimed in claim 1 where $R^3$ is chlorine or cyano.

4. A benzoic acid compound as claimed in claim 1 where X is oxygen.

5. A benzoic acid compound as claimed in claim 1 where $R^6$ is hydrogen.

6. A benzoic acid compound as claimed in claim 1 where $R^1$ is a heterocyclic radical of the formula II-A in which $R^{10}$ is $C_1$-$C_4$-alkyl or amino, $R^{11}$ is $C_1$-$C_4$-haloalkyl and $R^{12}$ is hydrogen.

7. A benzoic acid compound as claimed in claim 1 where $R^1$ is a heterocyclic radical of the formula II-B in which $R^{13}$ and $R^{13'}$ are each independently of one another $C_1$-$C_4$-alkyl.

8. A benzoic acid compound as claimed in claim 1 where $R^1$ is a heterocyclic radical of the formula II-C in which $R^{14}$ is fluorine or chlorine, $R^{15}$ is hydrogen and $R^{16}$ is $C_1$-$C_4$-haloalkyl, $C_1$-$C_4$-alkylsulfonyl or $C_1$-$C_4$-alkylsulfonyloxy.

9. A benzoic acid compound as claimed in claim 1 where R1 is a heterocyclic radical of the formula II-D in which $R^{18}$ is hydrogen, methyl or amino, $R^{19}$ is $C_1$-$C_4$-haloalkyl or $C_1$-$C_4$-alkylsulfonyl and $R^{19}$ is hydrogen.

10. A benzoic acid compound as claimed in claim 1 where
$R^2$ is hydrogen, chlorine or fluorine,
$R^3$ is chlorine or cyano,
$R^6$ is hydrogen and
X is oxygen.

11. A benzoic acid compound as claimed in claim 1 where $R^4$ or $R^5$ is hydrogen and the other radical $R^4$ or $R^5$ is $C_1$-$C_4$-alkyl or $R^4$, $R^5$ are each methyl.

12. A composition comprising a herbicidally effective amount of at least one 3-heterocyclyl-substituted benzoic acid compound of the formula I or an agriculturally useful salt thereof as claimed in claim 1 and at least one inert liquid and/or solid carrier and, if desired, at least one surfactant.

13. A composition for the desiccation/defoliation of plants, comprising an effective amount of at least one 3-heterocyclyl-substituted benzoic acid compound of the formula I or an agriculturally useful salt thereof as claimed in claim 1 which acts as a desiccant/defoliant and at least one inert liquid and/or solid carrier and, if desired, at least one surfactant.

14. A method for controlling unwanted vegetation, which comprises applying a herbicidally effective amount of at least one 3-heterocyclyl-substituted benzoic acid compound of the formula I or an agriculturally useful salt thereof as claimed in claim 1 to act on plants, their habitat and/or on seed.

15. A method for the desiccation/defoliation of plants, which comprises applying an amount which is effective as a desiccant/defoliant of at least one 3-heterocyclyl-substituted benzoic acid compound of the formula I or an agriculturally useful salt thereof as claimed in claim 1 to act on plants.

16. A method for controlling unwanted vegetation or for the desiccation/defoliation of plants, comprising applying to plants, the habitat of the plants or seeds of the plants an agriculturally effective amount of a compound or salt of claim 1.

* * * * *